US010916119B2

(12) United States Patent
Baker et al.

(10) Patent No.: US 10,916,119 B2
(45) Date of Patent: Feb. 9, 2021

(54) SYSTEM AND METHOD FOR CAREGIVER AVAILABILITY DETERMINATION

(71) Applicant: Hill-Rom Services, Inc., Batesville, IN (US)

(72) Inventors: Steven D. Baker, Beaverton, OR (US); Bradley T. Smith, Raleigh, NC (US); Eric D. Agdeppa, Cincinnati, OH (US); Pamela Wells, Hixson, TN (US); Laura A. Hassey, Raleigh, NC (US); Andrew S. Robinson, Durham, NC (US)

(73) Assignee: Hill-Rom Services, Inc., Batesville, IN (US)

( * ) Notice: Subject to any disclaimer, the term of this patent is extended or adjusted under 35 U.S.C. 154(b) by 0 days.

(21) Appl. No.: 16/695,573

(22) Filed: Nov. 26, 2019

(65) Prior Publication Data

US 2020/0211360 A1    Jul. 2, 2020

Related U.S. Application Data

(60) Provisional application No. 62/785,395, filed on Dec. 27, 2018.

(51) Int. Cl.
*G08B 25/00* (2006.01)
*H04W 4/029* (2018.01)
(Continued)

(52) U.S. Cl.
CPC ............ *G08B 25/005* (2013.01); *A61B 5/024* (2013.01); *A61B 5/0816* (2013.01); *A61B 5/746* (2013.01);
(Continued)

(58) Field of Classification Search
CPC combination set(s) only.
See application file for complete search history.

(56) References Cited

U.S. PATENT DOCUMENTS

| 5,534,851 A | 7/1996 | Russek |
| 5,594,786 A | 1/1997 | Chaco et al. |

(Continued)

FOREIGN PATENT DOCUMENTS

| CN | 102110347 A | 6/2011 |
| WO | WO 95/03596 A2 | 2/1995 |

(Continued)

OTHER PUBLICATIONS

Extended European Search Report for European Patent Application No. 19217152.8 dated May 11, 2020 (13 pages).
(Continued)

*Primary Examiner* — Steven S Kelley
(74) *Attorney, Agent, or Firm* — Barnes & Thornburg LLP

(57) ABSTRACT

A system and method to determine availability of caregivers to respond to nurse calls or other alerts originating in patient rooms is provided. Caregivers are designated as unavailable depending upon room types in which they are located, or depending upon patient types in the rooms in which they are located, or depending upon how long they have been present in certain rooms, or depending upon whether the caregivers have designated themselves as unavailable, or any combination of the foregoing. A system and method to escalate alerts to other caregivers if a primary caregiver is unavailable includes escalating first to a designated secondary caregiver and then to a caregiver who is closest in proximity to the room from which the alert originated if the secondary caregiver is also unavailable.

19 Claims, 3 Drawing Sheets

(51) Int. Cl.
*A61B 5/024* (2006.01)
*A61B 5/08* (2006.01)
*A61B 5/00* (2006.01)
*G08B 25/10* (2006.01)
*H04W 4/12* (2009.01)

(52) U.S. Cl.
CPC ............ *A61B 5/7465* (2013.01); *G08B 25/10* (2013.01); *H04W 4/029* (2018.02); *H04W 4/12* (2013.01)

(56) References Cited

U.S. PATENT DOCUMENTS

| | | | |
|---|---|---|---|
| 6,067,019 A | 5/2000 | Scott | |
| 6,208,250 B1 | 3/2001 | Dixon et al. | |
| 6,302,844 B1 | 10/2001 | Walker et al. | |
| 6,680,443 B2 | 1/2004 | Dixon | |
| 6,924,441 B1 | 8/2005 | Mobley et al. | |
| 6,982,639 B2* | 1/2006 | Brackett | H04W 4/021 340/539.13 |
| 7,176,391 B2 | 2/2007 | Metz et al. | |
| 7,253,366 B2 | 8/2007 | Bhai | |
| 7,319,386 B2 | 1/2008 | Collins, Jr. et al. | |
| 7,335,839 B2 | 2/2008 | Metz et al. | |
| 7,464,605 B2 | 12/2008 | Douglas et al. | |
| 7,752,926 B2 | 7/2010 | Caminade et al. | |
| 7,801,743 B2 | 9/2010 | Graves et al. | |
| 8,046,625 B2 | 10/2011 | Ferguson et al. | |
| 8,169,304 B2* | 5/2012 | Schuman, Sr. | G08B 7/06 340/286.07 |
| 8,252,679 B2 | 8/2012 | Liu | |
| 8,281,433 B2 | 10/2012 | Riley et al. | |
| 8,384,526 B2 | 2/2013 | Schuman, Sr. et al. | |
| 8,598,893 B2 | 12/2013 | Camus | |
| 8,598,995 B2 | 12/2013 | Schuman et al. | |
| 8,717,181 B2 | 5/2014 | Tallent et al. | |
| 8,779,924 B2 | 7/2014 | Pesot et al. | |
| 9,009,893 B2 | 4/2015 | Kramer et al. | |
| 9,286,441 B2 | 3/2016 | Zerhusen et al. | |
| 9,358,168 B2 | 6/2016 | Williamson et al. | |
| 9,383,251 B2 | 7/2016 | Dixon et al. | |
| 9,411,934 B2 | 8/2016 | Robinson et al. | |
| 9,517,034 B2* | 12/2016 | Collins, Jr. | A61G 7/1021 |
| 9,652,960 B2* | 5/2017 | Flinsenberg | G16H 40/20 |
| 10,672,260 B2* | 6/2020 | Al-Ali | G06F 11/30 |
| 2002/0165731 A1 | 11/2002 | Dempsey | |
| 2003/0013146 A1 | 1/2003 | Werb | |
| 2004/0078151 A1 | 4/2004 | Aljadeff et al. | |
| 2004/0125938 A1 | 7/2004 | Turcan et al. | |
| 2004/0125940 A1 | 7/2004 | Turcan et al. | |
| 2004/0193449 A1* | 9/2004 | Wildman | G16H 40/20 705/2 |
| 2005/0143671 A1 | 6/2005 | Hastings et al. | |
| 2005/0242928 A1 | 11/2005 | Kirkeby | |
| 2008/0018436 A1 | 1/2008 | Traughber et al. | |
| 2009/0040041 A1* | 2/2009 | Janetis | H04L 67/18 340/539.13 |
| 2009/0046837 A1 | 2/2009 | Thiel | |
| 2009/0058635 A1 | 3/2009 | LaLonde et al. | |
| 2012/0314901 A1 | 12/2012 | Hanson et al. | |
| 2013/0009778 A1* | 1/2013 | Bautovich | G08B 25/008 340/573.4 |
| 2013/0321145 A1* | 12/2013 | Ranieri | G16H 40/20 340/539.12 |
| 2014/0266642 A1* | 9/2014 | Girardeau | G16H 40/20 340/286.07 |
| 2015/0106121 A1* | 4/2015 | Muhsin | G16H 10/60 705/3 |
| 2015/0116112 A1 | 4/2015 | Flinsenberg et al. | |
| 2015/0199481 A1* | 7/2015 | Kowal | G06Q 10/00 705/2 |
| 2016/0012197 A1* | 1/2016 | Eromo | G06Q 10/10 705/2 |
| 2016/0029160 A1* | 1/2016 | Theurer | G01S 5/0284 455/456.1 |
| 2017/0364537 A1* | 12/2017 | Kariman | H04L 63/1433 |
| 2018/0082573 A1* | 3/2018 | Zuckerman | G08B 25/001 |
| 2018/0114288 A1* | 4/2018 | Aldaz | G06Q 10/10 |
| 2018/0184984 A1 | 7/2018 | Zerhusen et al. | |
| 2019/0108908 A1* | 4/2019 | Faulks | G16H 40/20 |
| 2019/0122760 A1* | 4/2019 | Wang | G06Q 10/02 |
| 2020/0185087 A1* | 6/2020 | Smith | G08B 3/1016 |

FOREIGN PATENT DOCUMENTS

| | | |
|---|---|---|
| WO | WO 2007/081823 A2 | 7/2007 |
| WO | WO 2013/164721 A1 | 11/2013 |
| WO | WO 2017/083353 A1 | 5/2017 |
| WO | 2018026988 A1 | 2/2018 |

OTHER PUBLICATIONS

"Recent Trends and Advances in UWB Positioning," by Mohamed R. Mahfouz et al.; Wireless Sensing, Local Positioning, and RFID, 2009. IMWS 2009. IEEE MTT-S International Microwave Workshop on, IEEE, Piscataway, 'NJ, USA, Sep. 24, 2009, pp. 1-4, XP031558925, ISBN: 978-1-4244-5060-2.

* cited by examiner

SYSTEM AND METHOD FOR CAREGIVER AVAILABILITY DETERMINATION The present application claims the benefit, under 35 U.S.C. § 119(e), to U.S. Provisional Patent Application No. 62/785,395, filed Dec. 27, 2018, which is hereby incorporated by reference herein in its entirety.

BACKGROUND

The present disclosure relates to locating systems and methods used in healthcare facilities to track the locations of caregivers, and more particularly, to systems and methods to determine caregiver unavailability in a healthcare facility. The present disclosure also relates to real time locating systems (RTLS's) used in healthcare facilities in conjunction with nurse call systems that receive alert calls.

In healthcare facilities, caregivers frequently receive nurse calls from patients, family members of the patients, or other caregivers to attend to patients in need. These nurse calls are oftentimes sent by pressing a nurse call button on a pillow speaker unit or on a hospital bed. Some nurse calls or alert calls also may be generated by equipment, such as patient beds in patient rooms. In some cases, one or more of the alert calls may be a high priority or time sensitive call, and attending to the respective patient as quickly as possible in response to the high priority alert call is desired. At the same time, sending messages regarding alert calls to caregivers who are not available to respond to the calls typically results in response delays until messages regarding the alert calls are escalated to other caregivers who are available to respond to the alert calls. Accordingly, there is room for improvement in systems and methods for routing alert calls to available caregivers and refraining from routing such alert calls to unavailable caregivers.

SUMMARY

An apparatus, system, or method may comprise one or more of the features recited in the appended claims and/or the following features which, alone or in any combination, may comprise patentable subject matter:

According to a first aspect of the present disclosure, a system may be provided to determine caregiver availability for responding to alert calls in a healthcare facility having a plurality of patient rooms. The system may include a plurality of locating tags each of which may be worn by a respective caregiver in the healthcare facility. Each locating tag may have tag identification data (ID) stored therein. Each locating tag may have a transmitter that may be configured to transmit the respective tag ID. The system may also have a plurality of transceivers that may be mounted at fixed locations throughout the healthcare facility. Each transceiver may be configured to receive the tag ID's from the plurality of locating tags that are within a communication range of the transceiver. Each transceiver may have a transceiver ID stored therein. The system further may have a locating server that may be communicatively coupled to the plurality of transceivers to receive the tag ID's and the transceiver ID's transmitted by the plurality of transceivers. The locating server may be configured to determine a location of each caregiver in the healthcare facility based on the tag ID's and the transceiver ID's. The system further may have a plurality of alert placement devices. At least one alert placement device of the plurality of alert placement devices may be located in each of the patient rooms of the plurality of patient rooms. Each alert placement device may be configured to send an alert call. Still further, the system may have a nurse call server that may be communicatively coupled to the plurality of alert placement devices to receive alert calls therefrom and that may be communicatively coupled to the locating server. The locating server or the nurse call server may be configured to determine which caregivers of the plurality of caregivers may be unavailable to respond to alert calls transmitted by the alert placement devices based on a type of patient assigned to each of the patient rooms in which each of the caregivers may be currently located as determined by the locating server.

In some embodiments of the first aspect, the system further may include a plurality of portable communication devices. Each portable communication device may be carried by a respective caregiver of the plurality of caregivers. Each portable communication device may be usable by the caregivers to designate themselves as unavailable.

Optionally, the plurality of alert placement devices of the first aspect may include pillow speaker units that each may have a nurse call button that may be selected by a respective patient to generate the alert call. Alternatively or additionally, the plurality of alert placement devices of the first aspect may include patient beds that each may have a nurse call button that may be selected by a respective patient to generate the alert call. Further alternatively or additionally, the plurality of alert placement devices of the first aspect may include patient beds and the alert calls may include bed status alerts that may be transmitted from the patient beds. For example, the bed status alert from each patient bed of the first aspect may include one or more of the following: a siderail position alert, a caster brake alert, a mattress alert, a bed lift system alert, a bed component temperature alert, a head of bed angle alert, or a bed height alert.

Further optionally, the plurality of alert placement devices of the first aspect may include patient beds that may include heart rate sensors and the alert calls may relate to sensed heart rate. Alternatively or additionally, the plurality of alert placement devices of the first aspect may comprise patient beds that may include respiration rate sensors and the alert calls may relate to sensed respiration rate. It is also contemplated by this disclosure that the system of the first aspect may further include a plurality of room stations. Each room station of the first aspect may be located in a respective patient room of the plurality of patient rooms and may be communicatively coupled to the nurse call server. The room stations of the first aspect, therefore, each may be usable to send a respective alert call.

In some embodiments of the first aspect, the system further may include portable communication devices that may be carried by the caregivers and each patient room may have a primary caregiver assigned thereto. The nurse call server may send an alert message to the portable communication device of the primary caregiver to notify the primary caregiver of any alert calls originating from any of the primary caregiver's assigned patient rooms if the primary caregiver has not been determined to be unavailable. According to the first aspect, each patient room may have a secondary caregiver assigned thereto and if the primary caregiver has been determined to be unavailable, the nurse call server may send an alert message to the portable communication device of the secondary caregiver to notify the secondary caregiver of any alert calls originating from any of the secondary caregiver's assigned patient rooms if the secondary caregiver has not been determined to be unavailable.

If the secondary caregiver has also been determined to be unavailable in the system of the first aspect, the nurse call server may send an alert message to the portable communication device of a closest caregiver, other than the primary and secondary caregiver, determined by the locating server to be closest to the patient room from which a respective alert call has originated if the closest caregiver has not been determined to be unavailable. If the closest caregiver has also been determined to be unavailable in the system of the first aspect, the nurse call server may send an alert message to the portable communication device of a next closest caregiver, other than the primary and secondary caregiver, determined by the locating server to be next closest to the patient room from which a respective alert call has originated if the next closest caregiver has not been determined to be unavailable.

Optionally, the nurse call server or the locating server of the first aspect may be configured also to designate caregivers as unavailable based on a qualification of the respective caregiver or the role of the respective caregiver. Further optionally, the nurse call server or the locating server of the first aspect may be configured also to designate caregivers as unavailable based on a distance between the respective caregiver and the patient room in which a respective alert call has originated exceeding a distance threshold.

In some embodiments of the system of the first aspect, the plurality of transceivers and the plurality of locating tags may communicate via ultra-wideband (UWB) signals. Furthermore, the location of the plurality of locating tags in the system of the first aspect may be determined by the locating server using two way ranging and/or time difference of arrival (TDOA) techniques. The locating server of the first aspect may use signals from only a subset of the plurality of transceivers to determine the location of each locating tag of the plurality of locating tags. The subset may be determined based on signal strength of UWB signals between the transceivers and the respective locating tag, for example. If desired, the subset may include at least three transceivers from the plurality of transceivers having highest signal strength values as compared to others of the plurality of transceivers.

It is contemplated by this disclosure with regard to the system according to the first aspect that the nurse call server or locating server further may be configured to designate caregivers as unavailable if the caregivers are located in predetermined non-patient room areas of the healthcare facility. The predetermined non-patient room areas of the hospital may include bathrooms, for example.

According to a second aspect of the present disclosure, a system may be provided to determine caregiver availability for responding to alert calls in a healthcare facility having a plurality of patient rooms. The system may include a plurality of locating tags each of which is worn by a respective caregiver in the healthcare facility. Each locating tag may have tag identification data (ID) stored therein. Each locating tag may have a transmitter that may be configured to transmit the respective tag ID. The system may also have a plurality of transceivers that may be mounted at fixed locations throughout the healthcare facility. Each transceiver may be configured to receive the tag ID's from the plurality of locating tags that are within a communication range of the transceiver. Each transceiver may have a transceiver ID stored therein. The system may further have a locating server that may be communicatively coupled to the plurality of transceivers to receive the tag ID's and the transceiver ID's transmitted by the plurality of transceivers. The locating server may be configured to determine a location of each caregiver in the healthcare facility based on the tag ID's and the transceiver ID's. The system further may have a plurality of alert placement devices. At least one alert placement device of the plurality of alert placement devices may be located in each of the patient rooms of the plurality of patient rooms. Each alert placement device may be configured to send an alert call. The system also may have a plurality of patient detectors. Each patient detector may be located in a respective patient room of the plurality of patient rooms. Each patient detector may be configured to detect a presence of a patient in the respective patient room. Each patient detector may be configured to send a patient presence signal. Still further, the system may have a nurse call server that may be communicatively coupled to the plurality of alert placement devices to receive alert calls therefrom and that may be coupled to the plurality of patient detectors. The nurse call server may also be communicatively coupled to the locating server. The locating server or the nurse call server may be configured to determine which caregivers of the plurality of caregivers may be unavailable to respond to alert calls transmitted by the alert placement devices based on a type of room in which each of the caregivers are located as determined by the locating server but the caregivers are only designated as unavailable if the respective patient detectors also detect that the patients are located in the patient rooms with the caregivers.

In some embodiments of the second aspect, the system further may include a plurality of portable communication devices. Each portable communication device may be carried by a respective caregiver of the plurality of caregivers. Each portable communication device may be usable by the caregivers to designate themselves as unavailable.

Optionally, the plurality of alert placement devices of the second aspect may include pillow speaker units that each may have a nurse call button that may be selected by a respective patient to generate the alert call. Alternatively or additionally, the plurality of alert placement devices of the second aspect may include patient beds that each may have a nurse call button that may be selected by a respective patient to generate the alert call. Further alternatively or additionally, the plurality of alert placement devices of the second aspect may include patient beds and the alert calls may include bed status alerts that may be transmitted from the patient beds. For example, the bed status alert from each patient bed of the second aspect may include one or more of the following: a siderail position alert, a caster brake alert, a mattress alert, a bed lift system alert, a bed component temperature alert, a head of bed angle alert, or a bed height alert.

Further optionally, the plurality of alert placement devices of the second aspect may include patient beds that may include heart rate sensors and the alert calls may relate to sensed heart rate. Alternatively or additionally, the plurality of alert placement devices of the second aspect may comprise patient beds that may include respiration rate sensors and the alert calls may relate to sensed respiration rate. It is also contemplated by this disclosure that the system of the second aspect may further include a plurality of room stations. Each room station of the second aspect may be located in a respective patient room of the plurality of patient rooms and may be communicatively coupled to the nurse call server. The room stations of the second aspect, therefore, each may be usable to send a respective alert call.

In some embodiments of the second aspect, the system further may include portable communication devices that may be carried by the caregivers and each patient room may have a primary caregiver assigned thereto. The nurse call server may send an alert message to the portable communication device of the primary caregiver to notify the primary caregiver of any alert calls originating from any of the primary caregiver's assigned patient rooms if the primary caregiver has not been determined to be unavailable. According to the second aspect, each patient room may have a secondary caregiver assigned thereto and if the primary caregiver has been determined to be unavailable, the nurse call server may send an alert message to the portable communication device of the secondary caregiver to notify the secondary caregiver of any alert calls originating from any of the secondary caregiver's assigned patient rooms if the secondary caregiver has not been determined to be unavailable.

If the secondary caregiver has also been determined to be unavailable in the system of the second aspect, the nurse call server may send an alert message to the portable communication device of a closest caregiver, other than the primary and secondary caregiver, determined by the locating server to be closest to the patient room from which a respective alert call has originated if the closest caregiver has not been determined to be unavailable. If the closest caregiver has also been determined to be unavailable in the system of the second aspect, the nurse call server may send an alert message to the portable communication device of a next closest caregiver, other than the primary and secondary caregiver, determined by the locating server to be next closest to the patient room from which a respective alert call has originated if the next closest caregiver has not been determined to be unavailable.

Optionally, the nurse call server or the locating server of the second aspect may be configured also to designate caregivers as unavailable based on a qualification of the respective caregiver or the role of the respective caregiver. Further optionally, the nurse call server or the locating server of the second aspect may be configured also to designate caregivers as unavailable based on a distance between the respective caregiver and the patient room in which a respective alert call has originated exceeding a distance threshold.

In some embodiments of the system of the second aspect, the plurality of transceivers and the plurality of locating tags may communicate via ultra-wideband (UWB) signals. Furthermore, the location of the plurality of locating tags in the system of the second aspect may be determined by the locating server using two way ranging and/or time difference of arrival (TDOA) techniques. The locating server of the second aspect may use signals from only a subset of the plurality of transceivers to determine the location of each locating tag of the plurality of locating tags. The subset may be determined based on signal strength of UWB signals between the transceivers and the respective locating tag, for example. If desired, the subset may include at least three transceivers from the plurality of transceivers having highest signal strength values as compared to others of the plurality of transceivers.

It is contemplated by this disclosure with regard to the system according to the second aspect that the nurse call server or locating server further may be configured to designate caregivers as unavailable if the caregivers are located in predetermined non-patient room areas of the healthcare facility. The predetermined non-patient room areas of the hospital may include bathrooms, for example.

In some embodiments of the second aspect, the patient detectors may include one or more sensors that may be included in respective patient beds that may be located in the corresponding patient rooms. For example, the one or more sensors of the second aspect may include one or more weight sensors that may detect a weight of the patient when the patient is supported on the patient bed.

According to a third aspect of the present disclosure, a system may be provided to determine caregiver availability for responding to alert calls in a healthcare facility having a plurality of patient rooms. The system may include a plurality of locating tags each of which may be worn by a respective caregiver and a respective patient in the healthcare facility. Each locating tag may have tag identification data (ID) stored therein. Each locating tag may have a transmitter configured to transmit the respective tag ID. The system may also have a plurality of transceivers that may be mounted at fixed locations throughout the healthcare facility. Each transceiver may be configured to receive the tag ID's from the plurality of locating tags that are within a communication range of the transceiver. Each transceiver may have a transceiver ID stored therein. The system may further have a locating server that may be communicatively coupled to the plurality of transceivers to receive the tag ID's and the transceiver ID's transmitted by the plurality of transceivers. The locating server may be configured to determine a location of each caregiver and each patient in the healthcare facility based on the tag ID's and the transceiver ID's. The system further may have a plurality of alert placement devices. At least one alert placement device of the plurality of alert placement devices may be located in each of the patient rooms of the plurality of patient rooms. Each alert placement device may be configured to send an alert call. Still further, the system may have a nurse call server that may be communicatively coupled to the plurality of alert placement devices to receive alert calls therefrom and that may be communicatively coupled to the locating server. The locating server or the nurse call server may be configured to determine which caregivers of the plurality of caregivers may be unavailable to respond to alert calls transmitted by the alert placement devices based on a type of room in which each of the caregivers are located as determined by the locating server but the caregivers are only designated as unavailable if the respective patients are also determined by the locating server to be located in the patient rooms with the caregivers.

In some embodiments of the third aspect, the system further may include a plurality of portable communication devices. Each portable communication device may be carried by a respective caregiver of the plurality of caregivers. Each portable communication device may be usable by the caregivers to designate themselves as unavailable.

Optionally, the plurality of alert placement devices of the third aspect may include pillow speaker units that each may have a nurse call button that may be selected by a respective patient to generate the alert call. Alternatively or additionally, the plurality of alert placement devices of the third aspect may include patient beds that each may have a nurse call button that may be selected by a respective patient to generate the alert call. Further alternatively or additionally, the plurality of alert placement devices of the third aspect may include patient beds and the alert calls may include bed status alerts that may be transmitted from the patient beds. For example, the bed status alert from each patient bed of the third aspect may include one or more of the following: a siderail position alert, a caster brake alert, a mattress alert, a bed lift system alert, a bed component temperature alert, a head of bed angle alert, or a bed height alert.

Further optionally, the plurality of alert placement devices of the third aspect may include patient beds that may include heart rate sensors and the alert calls may relate to sensed heart rate. Alternatively or additionally, the plurality of alert placement devices of the third aspect may comprise patient beds that may include respiration rate sensors and the alert calls may relate to sensed respiration rate. It is also contemplated by this disclosure that the system of the third aspect may further include a plurality of room stations. Each room station of the third aspect may be located in a respective patient room of the plurality of patient rooms and may be communicatively coupled to the nurse call server. The room stations of the third aspect, therefore, each may be usable to send a respective alert call.

In some embodiments of the third aspect, the system further may include portable communication devices that may be carried by the caregivers and each patient room may have a primary caregiver assigned thereto. The nurse call server may send an alert message to the portable communication device of the primary caregiver to notify the primary caregiver of any alert calls originating from any of the primary caregiver's assigned patient rooms if the primary caregiver has not been determined to be unavailable. According to the third aspect, each patient room may have a secondary caregiver assigned thereto and if the primary caregiver has been determined to be unavailable, the nurse call server may send an alert message to the portable communication device of the secondary caregiver to notify the secondary caregiver of any alert calls originating from any of the secondary caregiver's assigned patient rooms if the secondary caregiver has not been determined to be unavailable.

If the secondary caregiver has also been determined to be unavailable in the system of the third aspect, the nurse call server may send an alert message to the portable communication device of a closest caregiver, other than the primary and secondary caregiver, determined by the locating server to be closest to the patient room from which a respective alert call has originated if the closest caregiver has not been determined to be unavailable. If the closest caregiver has also been determined to be unavailable in the system of the third aspect, the nurse call server may send an alert message to the portable communication device of a next closest caregiver, other than the primary and secondary caregiver, determined by the locating server to be next closest to the patient room from which a respective alert call has originated if the next closest caregiver has not been determined to be unavailable.

Optionally, the nurse call server or the locating server of the third aspect may be configured also to designate caregivers as unavailable based on a qualification of the respective caregiver or the role of the respective caregiver. Further optionally, the nurse call server or the locating server of the third aspect may be configured also to designate caregivers as unavailable based on a distance between the respective caregiver and the patient room in which a respective alert call has originated exceeding a distance threshold.

In some embodiments of the system of the third aspect, the plurality of transceivers and the plurality of locating tags may communicate via ultra-wideband (UWB) signals. Furthermore, the location of the plurality of locating tags in the system of the third aspect may be determined by the locating server using two way ranging and/or time difference of arrival (TDOA) techniques. The locating server of the third aspect may use signals from only a subset of the plurality of transceivers to determine the location of each locating tag of the plurality of locating tags. The subset may be determined based on signal strength of UWB signals between the transceivers and the respective locating tag, for example. If desired, the subset may include at least three transceivers from the plurality of transceivers having highest signal strength values as compared to others of the plurality of transceivers.

It is contemplated by this disclosure with regard to the system according to the third aspect that the nurse call server or locating server further may be configured to designate caregivers as unavailable if the caregivers are located in predetermined non-patient room areas of the healthcare facility. The predetermined non-patient room areas of the hospital may include bathrooms, for example.

According to a fourth aspect of the present disclosure, a system may be provided to determine caregiver availability for responding to alert calls in a healthcare facility having a plurality of patient rooms. The system may include a plurality of locating tags each of which may be worn by a respective caregiver in the healthcare facility. Each locating tag may have tag identification data (ID) stored therein. Each locating tag may have a transmitter that may be configured to transmit the respective tag ID. The system may also have a plurality of transceivers that may be mounted at fixed locations throughout the healthcare facility. Each transceiver may be configured to receive the tag ID's from the plurality of locating tags that are within a communication range of the transceiver. Each transceiver may have a transceiver ID stored therein. The system may further have a locating server communicatively that may be coupled to the plurality of transceivers to receive the tag ID's and the transceiver ID's transmitted by the plurality of transceivers. The locating server may be configured to determine a location of each caregiver in the healthcare facility based on the tag ID's and the transceiver ID's. The system further may have a plurality of alert placement devices. At least one alert placement device of the plurality of alert placement devices may be located in each of the patient rooms of the plurality of patient rooms. Each alert placement device may be configured to send an alert call. Still further, the system may have a nurse call server that may be communicatively coupled to the plurality of alert placement devices to receive alert calls therefrom and that may be communicatively coupled to the locating server. The locating server or the nurse call server may be configured to determine which caregivers of the plurality of caregivers may be unavailable to respond to alert calls transmitted by the alert placement devices based on a type of room in which each of the caregivers are located as determined by the locating server but only after the respective caregivers have been located in the respective patient rooms for a threshold period of time.

In some embodiments of the fourth aspect, the system further may include a plurality of portable communication devices. Each portable communication device may be carried by a respective caregiver of the plurality of caregivers. Each portable communication device may be usable by the caregivers to designate themselves as unavailable.

Optionally, the plurality of alert placement devices of the fourth aspect may include pillow speaker units that each may have a nurse call button that may be selected by a respective patient to generate the alert call. Alternatively or additionally, the plurality of alert placement devices of the fourth aspect may include patient beds that each may have a nurse call button that may be selected by a respective patient to generate the alert call. Further alternatively or additionally, the plurality of alert placement devices of the fourth aspect may include patient beds and the alert calls may include bed status alerts that may be transmitted from the patient beds. For example, the bed status alert from each patient bed of the fourth aspect may include one or more of the following: a siderail position alert, a caster brake alert, a mattress alert, a bed lift system alert, a bed component temperature alert, a head of bed angle alert, or a bed height alert.

Further optionally, the plurality of alert placement devices of the fourth aspect may include patient beds that may include heart rate sensors and the alert calls may relate to sensed heart rate. Alternatively or additionally, the plurality of alert placement devices of the fourth aspect may comprise patient beds that may include respiration rate sensors and the alert calls may relate to sensed respiration rate. It is also contemplated by this disclosure that the system of the fourth aspect may further include a plurality of room stations. Each room station of the fourth aspect may be located in a respective patient room of the plurality of patient rooms and may be communicatively coupled to the nurse call server. The room stations of the fourth aspect, therefore, each may be usable to send a respective alert call.

In some embodiments of the fourth aspect, the system further may include portable communication devices that may be carried by the caregivers and each patient room may have a primary caregiver assigned thereto. The nurse call server may send an alert message to the portable communication device of the primary caregiver to notify the primary caregiver of any alert calls originating from any of the primary caregiver's assigned patient rooms if the primary caregiver has not been determined to be unavailable. According to the fourth aspect, each patient room may have a secondary caregiver assigned thereto and if the primary caregiver has been determined to be unavailable, the nurse call server may send an alert message to the portable communication device of the secondary caregiver to notify the secondary caregiver of any alert calls originating from any of the secondary caregiver's assigned patient rooms if the secondary caregiver has not been determined to be unavailable.

If the secondary caregiver has also been determined to be unavailable in the system of the fourth aspect, the nurse call server may send an alert message to the portable communication device of a closest caregiver, other than the primary and secondary caregiver, determined by the locating server to be closest to the patient room from which a respective alert call has originated if the closest caregiver has not been determined to be unavailable. If the closest caregiver has also been determined to be unavailable in the system of the fourth aspect, the nurse call server may send an alert message to the portable communication device of a next closest caregiver, other than the primary and secondary caregiver, determined by the locating server to be next closest to the patient room from which a respective alert call has originated if the next closest caregiver has not been determined to be unavailable.

Optionally, the nurse call server or the locating server of the fourth aspect may be configured also to designate caregivers as unavailable based on a qualification of the respective caregiver or the role of the respective caregiver. Further optionally, the nurse call server or the locating server of the fourth aspect may be configured also to designate caregivers as unavailable based on a distance between the respective caregiver and the patient room in which a respective alert call has originated exceeding a distance threshold.

In some embodiments of the system of the fourth aspect, the plurality of transceivers and the plurality of locating tags may communicate via ultra-wideband (UWB) signals. Furthermore, the location of the plurality of locating tags in the system of the fourth aspect may be determined by the locating server using two way ranging and/or time difference of arrival (TDOA) techniques. The locating server of the fourth aspect may use signals from only a subset of the plurality of transceivers to determine the location of each locating tag of the plurality of locating tags. The subset may be determined based on signal strength of UWB signals between the transceivers and the respective locating tag, for example. If desired, the subset may include at least three transceivers from the plurality of transceivers having highest signal strength values as compared to others of the plurality of transceivers.

It is contemplated by this disclosure with regard to the system according to the fourth aspect that the nurse call server or locating server further may be configured to designate caregivers as unavailable if the caregivers are located in predetermined non-patient room areas of the healthcare facility. The predetermined non-patient room areas of the hospital may include bathrooms, for example.

According to a fifth aspect of the present disclosure, a method may be provided to determine caregiver availability for responding to alert calls in a healthcare facility having a plurality of patient rooms. The method of the fifth aspect may include transmitting tag identification data (tag ID's) from a transmitter of a plurality of locating tags each of which may be worn by a respective caregiver in the healthcare facility. The method further may include, at a plurality of transceivers that may be mounted at fixed locations throughout the healthcare facility, receiving the tag ID's from the plurality of locating tags that are within a communication range of the respective transceiver. Each transceiver may have a transceiver ID stored therein. The method may also include, at a locating server that may be communicatively coupled to the plurality of transceivers, receiving the tag ID's and the transceiver ID's transmitted by the plurality of transceivers. The method may further include determining at the locating server a location of each caregiver in the healthcare facility based on the tag ID's and the transceiver ID's. Still further, the method may include sending one or more alert calls from a plurality of alert placement devices. At least one alert placement device of the plurality of alert placement devices may be located in each of the patient rooms of the plurality of patient rooms. The method may further include, at a nurse call server that may be communicatively coupled to the plurality of alert placement devices and that may be communicatively coupled to the locating server, receiving the alert calls from the alert placement devices. Also, the method may include, at the locating server or the nurse call server, determining which caregivers of the plurality of caregivers may be unavailable to respond to alert calls transmitted by the alert placement devices based on a type of patient assigned to each of the patient rooms in which each of the caregivers may be currently located as determined by the locating server.

In some embodiments of the fifth aspect, the method further includes receiving from a plurality of portable communication devices, each of which may be carried by a respective caregiver of the plurality of caregivers, a message that may be sent by the caregivers to designate themselves as unavailable. Optionally, sending one or more alert calls from the plurality of alert placement devices of the fifth aspect may include selecting a nurse call button of a pillow speaker unit. Alternatively or additionally, sending one or more alert calls from the plurality of alert placement devices of the fifth aspect may include selecting a nurse call button of a patient bed. Further alternatively or additionally, sending one or more alert calls from the plurality of alert placement devices of the fifth aspect may include transmitting one or more bed status alerts from a patient bed. For example, the one or more bed status alerts from the patient bed may include one or more of the following: a siderail position alert, a caster brake alert, a mattress alert, a bed lift system alert, a bed component temperature alert, a head of bed angle alert, or a bed height alert.

In some embodiments of the method of the fifth aspect, sending one or more alert calls from the plurality of alert placement devices may include sending an alert related to sensed heart rate from a patient bed including a heart rate sensor. Alternatively or additionally, sending one or more alert calls from the plurality of alert placement devices of the fifth aspect may include sending an alert related to sensed respiration rate from a patient bed including a respiration rate sensor. Further alternatively or additionally, sending one or more alert calls from the plurality of alert placement devices of the fifth aspect may include sending an alert from a room station of a plurality of room stations. Each room station may be located in a respective patient room of the plurality of patient rooms and may be communicatively coupled to the nurse call server in the method of the fifth aspect.

It is contemplated by the present disclosure that the method of the fifth aspect may further include assigning to each patient room a primary caregiver and sending an alert message from the nurse call server to a portable communication device of the primary caregiver to notify the primary caregiver of any alert calls originating from any of the primary caregiver's assigned patient rooms if the primary caregiver has not been determined to be unavailable. Optionally, the method the fifth aspect may further include assigning to each patient room a secondary caregiver and, if the primary caregiver has been determined to be unavailable, sending an alert message from the nurse call server to a portable communication device of the secondary caregiver to notify the secondary caregiver of any alert calls originating from any of the secondary caregiver's assigned patient rooms if the secondary caregiver has not been determined to be unavailable.

In some embodiments of the fifth aspect, if the secondary caregiver has also been determined to be unavailable, the method includes sending an alert message from the nurse call server to a portable communication device of a closest caregiver, other than the primary and secondary caregiver, as determined by the locating server to be closest to the patient room from which a respective alert call has originated if the closest caregiver has not been determined to be unavailable. If the closest caregiver has also been determined to be unavailable in the fifth aspect, the method may further include sending an alert message from the nurse call server to the portable communication device of a next closest caregiver, other than the primary and secondary caregiver, as determined by the locating server to be next closest to the patient room from which a respective alert call has originated if the next closest caregiver has not been determined to be unavailable.

Optionally, the method of the fifth aspect may include, with the nurse call server or the locating server, designating one or more caregivers as unavailable based on a qualification of the respective caregiver or the role of the respective caregiver. Alternatively or additionally, the method of the fifth aspect may include, with the nurse call server or the locating server, designating one or more caregivers as unavailable based on a distance between the respective caregiver and the patient room in which a respective alert call has originated exceeding a distance threshold.

In embodiments of the method of the fifth aspect, the plurality of transceivers and the plurality of locating tags may communicate via ultra-wideband (UWB) signals. Furthermore, the location of the plurality of locating tags in the method of the fifth aspect may be determined by the locating server using two way ranging and/or time difference of arrival (TDOA) techniques. The locating server of the fifth aspect may use signals from only a subset of the plurality of transceivers to determine the location of each locating tag of the plurality of locating tags. The subset may be determined based on signal strength of UWB signals between the transceivers and the respective locating tag, for example. If desired, the subset may include at least three transceivers from the plurality of transceivers having highest signal strength values as compared to others of the plurality of transceivers.

If desired, the method of the fifth aspect may further include, with the nurse call server or locating server, designating one or more caregivers as unavailable if the caregivers are located in predetermined non-patient room areas of the healthcare facility. For example, the predetermined non-patient room areas of the hospital may include bathrooms.

According to a sixth aspect of the present disclosure, a method may be provided to determine caregiver availability for responding to alert calls in a healthcare facility having a plurality of patient rooms. The method of the sixth aspect may include transmitting tag identification data (tag ID's) from a transmitter of a plurality of locating tags each of which may be worn by a respective caregiver in the healthcare facility. The method further may include, at a plurality of transceivers that may be mounted at fixed locations throughout the healthcare facility, receiving the tag ID's from the plurality of locating tags that are within a communication range of the respective transceiver. Each transceiver may have a transceiver ID stored therein. The method may also include, at a locating server that may be communicatively coupled to the plurality of transceivers, receiving the tag ID's and the transceiver ID's transmitted by the plurality of transceivers. The method may further include determining at the locating server a location of each caregiver in the healthcare facility based on the tag ID's and the transceiver ID's. Still further, the method may include sending one or more alert calls from a plurality of alert placement devices. At least one alert placement device of the plurality of alert placement devices may be located in each of the patient rooms of the plurality of patient rooms. The method may further include, with a plurality of patient detectors, detecting a presence of a patient in one or more patient rooms of the plurality of patient rooms and sending a patient presence signal from one or more of the plurality of patient detectors. Each patient detector may be located in a respective patient room of the plurality of patient rooms. The method may include, at a nurse call server that may be communicatively coupled to (i) the plurality of alert placement devices, (ii) the plurality of patient detectors, and (iii) the locating server, receiving the alert calls from the alert placement devices and receiving the patient presence signals from one or more of the plurality of patient detectors. Also, the method may include, at the locating server or the nurse call server, determining which caregivers of the plurality of caregivers may be unavailable to respond to alert calls transmitted by the alert placement devices based on a type of room in which each of the caregivers are located as determined by the locating server but the caregivers are only designated as unavailable if the respective patient detectors also detect that the patients are located in the patient rooms with the caregivers.

In some embodiments of the sixth aspect, the method further includes receiving from a plurality of portable communication devices, each of which may be carried by a respective caregiver of the plurality of caregivers, a message that may be sent by the caregivers to designate themselves as unavailable. Optionally, sending one or more alert calls from the plurality of alert placement devices of the sixth aspect may include selecting a nurse call button of a pillow speaker unit. Alternatively or additionally, sending one or more alert calls from the plurality of alert placement devices of the sixth aspect may include selecting a nurse call button of a patient bed. Further alternatively or additionally, sending one or more alert calls from the plurality of alert placement devices of the sixth aspect may include transmitting one or more bed status alerts from a patient bed. For example, the one or more bed status alerts from the patient bed may include one or more of the following: a siderail position alert, a caster brake alert, a mattress alert, a bed lift system alert, a bed component temperature alert, a head of bed angle alert, or a bed height alert.

In some embodiments of the method of the sixth aspect, sending one or more alert calls from the plurality of alert placement devices may include sending an alert related to sensed heart rate from a patient bed including a heart rate sensor. Alternatively or additionally, sending one or more alert calls from the plurality of alert placement devices of the sixth aspect may include sending an alert related to sensed respiration rate from a patient bed including a respiration rate sensor. Further alternatively or additionally, sending one or more alert calls from the plurality of alert placement devices of the sixth aspect may include sending an alert from a room station of a plurality of room stations. Each room station may be located in a respective patient room of the plurality of patient rooms and may be communicatively coupled to the nurse call server in the method of the sixth aspect.

It is contemplated by the present disclosure that the method of the sixth aspect may further include assigning to each patient room a primary caregiver and sending an alert message from the nurse call server to a portable communication device of the primary caregiver to notify the primary caregiver of any alert calls originating from any of the primary caregiver's assigned patient rooms if the primary caregiver has not been determined to be unavailable. Optionally, the method the sixth aspect may further include assigning to each patient room a secondary caregiver and, if the primary caregiver has been determined to be unavailable, sending an alert message from the nurse call server to a portable communication device of the secondary caregiver to notify the secondary caregiver of any alert calls originating from any of the secondary caregiver's assigned patient rooms if the secondary caregiver has not been determined to be unavailable.

In some embodiments of the sixth aspect, if the secondary caregiver has also been determined to be unavailable, the method includes sending an alert message from the nurse call server to a portable communication device of a closest caregiver, other than the primary and secondary caregiver, as determined by the locating server to be closest to the patient room from which a respective alert call has originated if the closest caregiver has not been determined to be unavailable. If the closest caregiver has also been determined to be unavailable in the sixth aspect, the method may further include sending an alert message from the nurse call server to the portable communication device of a next closest caregiver, other than the primary and secondary caregiver, as determined by the locating server to be next closest to the patient room from which a respective alert call has originated if the next closest caregiver has not been determined to be unavailable.

Optionally, the method of the sixth aspect may include, with the nurse call server or the locating server, designating one or more caregivers as unavailable based on a qualification of the respective caregiver or the role of the respective caregiver. Alternatively or additionally, the method of the sixth aspect may include, with the nurse call server or the locating server, designating one or more caregivers as unavailable based on a distance between the respective caregiver and the patient room in which a respective alert call has originated exceeding a distance threshold.

In some embodiments of the method of the sixth aspect, the plurality of transceivers and the plurality of locating tags may communicate via ultra-wideband (UWB) signals. Furthermore, the location of the plurality of locating tags in the method of the sixth aspect may be determined by the locating server using two way ranging and/or time difference of arrival (TDOA) techniques. The locating server of the sixth aspect may use signals from only a subset of the plurality of transceivers to determine the location of each locating tag of the plurality of locating tags. The subset may be determined based on signal strength of UWB signals between the transceivers and the respective locating tag, for example. If desired, the subset may include at least three transceivers from the plurality of transceivers having highest signal strength values as compared to others of the plurality of transceivers.

If desired, the method of the sixth aspect may further include, with the nurse call server or locating server, designating one or more caregivers as unavailable if the caregivers are located in predetermined non-patient room areas of the healthcare facility. For example, the predetermined non-patient room areas of the hospital may include bathrooms.

In some embodiments of the sixth aspect, the patient detectors may include one or more sensors included in respective patient beds that may be located in the corresponding patient rooms. For example, the one or more sensors of the sixth aspect may include one or more weight sensors that may detect a weight of the patient when the patient is supported on the patient bed.

According to a seventh aspect of the present disclosure, a method may be provided to determine caregiver availability for responding to alert calls in a healthcare facility having a plurality of patient rooms. The method of the seventh aspect may include transmitting tag identification data (tag ID's) from a transmitter of a plurality of locating tags each of which may be worn by a respective caregiver and a respective patient in the healthcare facility. The method further may include, at a plurality of transceivers that may be mounted at fixed locations throughout the healthcare facility, receiving the tag ID's from the plurality of locating tags that are within a communication range of the transceiver. Each transceiver may have a transceiver ID stored therein. The method may also include, at a locating server that may be communicatively coupled to the plurality of transceivers, receiving the tag ID's and the transceiver ID's transmitted by the plurality of transceivers. The method may further include determining at the locating server a location of each caregiver and each patient in the healthcare facility based on the tag ID's and the transceiver ID's. Still further, the method ma include sending one or more alert calls from a plurality of alert placement devices. At least one alert placement device of the plurality of alert placement devices may be located in each of the patient rooms of the plurality of patient rooms. The method may further include, at a nurse call server that may be communicatively coupled to the plurality of alert placement devices and that may be communicatively coupled to the locating server, receiving the alert calls from the alert placement devices. Also, the method may include, at the locating server or the nurse call server, determining which caregivers of the plurality of caregivers may be unavailable to respond to alert calls transmitted by the alert placement devices based on a type of room in which each of the caregivers are located as determined by the locating server but the caregivers are only designated as unavailable if the respective patients are also determined by the locating server to be located in the patient rooms with the caregivers.

In some embodiments of the seventh aspect, the method further includes receiving from a plurality of portable communication devices, each of which may be carried by a respective caregiver of the plurality of caregivers, a message that may be sent by the caregivers to designate themselves as unavailable. Optionally, sending one or more alert calls from the plurality of alert placement devices of the seventh aspect may include selecting a nurse call button of a pillow speaker unit. Alternatively or additionally, sending one or more alert calls from the plurality of alert placement devices of the seventh aspect may include selecting a nurse call button of a patient bed. Further alternatively or additionally, sending one or more alert calls from the plurality of alert placement devices of the seventh aspect may include transmitting one or more bed status alerts from a patient bed. For example, the one or more bed status alerts from the patient bed may include one or more of the following: a siderail position alert, a caster brake alert, a mattress alert, a bed lift system alert, a bed component temperature alert, a head of bed angle alert, or a bed height alert.

In some embodiments of the method of the seventh aspect, sending one or more alert calls from the plurality of alert placement devices may include sending an alert related to sensed heart rate from a patient bed including a heart rate sensor. Alternatively or additionally, sending one or more alert calls from the plurality of alert placement devices of the seventh aspect may include sending an alert related to sensed respiration rate from a patient bed including a respiration rate sensor. Further alternatively or additionally, sending one or more alert calls from the plurality of alert placement devices of the seventh aspect may include sending an alert from a room station of a plurality of room stations. Each room station may be located in a respective patient room of the plurality of patient rooms and may be communicatively coupled to the nurse call server in the method of the seventh aspect.

It is contemplated by the present disclosure that the method of the seventh aspect may further include assigning to each patient room a primary caregiver and sending an alert message from the nurse call server to a portable communication device of the primary caregiver to notify the primary caregiver of any alert calls originating from any of the primary caregiver's assigned patient rooms if the primary caregiver has not been determined to be unavailable. Optionally, the method the seventh aspect may further include assigning to each patient room a secondary caregiver and, if the primary caregiver has been determined to be unavailable, sending an alert message from the nurse call server to a portable communication device of the secondary caregiver to notify the secondary caregiver of any alert calls originating from any of the secondary caregiver's assigned patient rooms if the secondary caregiver has not been determined to be unavailable.

In some embodiments of the seventh aspect, if the secondary caregiver has also been determined to be unavailable, the method includes sending an alert message from the nurse call server to a portable communication device of a closest caregiver, other than the primary and secondary caregiver, as determined by the locating server to be closest to the patient room from which a respective alert call has originated if the closest caregiver has not been determined to be unavailable. If the closest caregiver has also been determined to be unavailable in the seventh aspect, the method may further include sending an alert message from the nurse call server to the portable communication device of a next closest caregiver, other than the primary and secondary caregiver, as determined by the locating server to be next closest to the patient room from which a respective alert call has originated if the next closest caregiver has not been determined to be unavailable.

Optionally, the method of the seventh aspect may include, with the nurse call server or the locating server, designating one or more caregivers as unavailable based on a qualification of the respective caregiver or the role of the respective caregiver. Alternatively or additionally, the method of the seventh aspect may include, with the nurse call server or the locating server, designating one or more caregivers as unavailable based on a distance between the respective caregiver and the patient room in which a respective alert call has originated exceeding a distance threshold.

In some embodiments of the method of the seventh aspect, the plurality of transceivers and the plurality of locating tags may communicate via ultra-wideband (UWB) signals. Furthermore, the location of the plurality of locating tags in the method of the seventh aspect may be determined by the locating server using two way ranging and/or time difference of arrival (TDOA) techniques. The locating server of the seventh aspect may use signals from only a subset of the plurality of transceivers to determine the location of each locating tag of the plurality of locating tags. The subset may be determined based on signal strength of UWB signals between the transceivers and the respective locating tag, for example. If desired, the subset may include at least three transceivers from the plurality of transceivers having highest signal strength values as compared to others of the plurality of transceivers.

If desired, the method of the seventh aspect may further include, with the nurse call server or locating server, designating one or more caregivers as unavailable if the caregivers are located in predetermined non-patient room areas of the healthcare facility. For example, the predetermined non-patient room areas of the hospital may include bathrooms.

According to an eighth aspect of the present disclosure, a method may be provided to determine caregiver availability for responding to alert calls in a healthcare facility having a plurality of patient rooms. The method of the eighth aspect may include transmitting tag identification data (tag ID's) from a transmitter of a plurality of locating tags each of which may be worn by a respective caregiver in the healthcare facility. The method further may include, at a plurality of transceivers that may be mounted at fixed locations throughout the healthcare facility, receiving the tag ID's from the plurality of locating tags that are within a communication range of the respective transceiver. Each transceiver may have a transceiver ID stored therein. The method may also include, at a locating server that may be communicatively coupled to the plurality of transceivers, receiving the tag ID's and the transceiver ID's transmitted by the plurality of transceivers. The method may further include determining at the locating server a location of each caregiver in the healthcare facility based on the tag ID's and the transceiver ID's. Still further the method may include sending one or more alert calls from a plurality of alert placement devices. At least one alert placement device of the plurality of alert placement devices may be located in each of the patient rooms of the plurality of patient rooms. The method may further include, at a nurse call server that may be communicatively coupled to the plurality of alert placement devices and that may be communicatively coupled to the locating server, receiving the alert calls from the alert placement devices. Also, the method may include, at the locating server or the nurse call server, determining which caregivers of the plurality of caregivers may be unavailable to respond to alert calls transmitted by the alert placement devices based on a type of room in which each of the caregivers are located as determined by the locating server but only after the respective caregivers have been located in the respective patient rooms for a threshold period of time.

In some embodiments of the eighth aspect, the method further includes receiving from a plurality of portable communication devices, each of which may be carried by a respective caregiver of the plurality of caregivers, a message that may be sent by the caregivers to designate themselves as unavailable. Optionally, sending one or more alert calls from the plurality of alert placement devices of the eighth aspect may include selecting a nurse call button of a pillow speaker unit. Alternatively or additionally, sending one or more alert calls from the plurality of alert placement devices of the eighth aspect may include selecting a nurse call button of a patient bed. Further alternatively or additionally, sending one or more alert calls from the plurality of alert placement devices of the eighth aspect may include transmitting one or more bed status alerts from a patient bed. For example, the one or more bed status alerts from the patient bed may include one or more of the following: a siderail position alert, a caster brake alert, a mattress alert, a bed lift system alert, a bed component temperature alert, a head of bed angle alert, or a bed height alert.

In some embodiments of the method of the eighth aspect, sending one or more alert calls from the plurality of alert placement devices may include sending an alert related to sensed heart rate from a patient bed including a heart rate sensor. Alternatively or additionally, sending one or more alert calls from the plurality of alert placement devices of the eighth aspect may include sending an alert related to sensed respiration rate from a patient bed including a respiration rate sensor. Further alternatively or additionally, sending one or more alert calls from the plurality of alert placement devices of the eighth aspect may include sending an alert from a room station of a plurality of room stations. Each room station may be located in a respective patient room of the plurality of patient rooms and may be communicatively coupled to the nurse call server in the method of the eighth aspect.

It is contemplated by the present disclosure that the method of the eighth aspect may further include assigning to each patient room a primary caregiver and sending an alert message from the nurse call server to a portable communication device of the primary caregiver to notify the primary caregiver of any alert calls originating from any of the primary caregiver's assigned patient rooms if the primary caregiver has not been determined to be unavailable. Optionally, the method the eighth aspect may further include assigning to each patient room a secondary caregiver and, if the primary caregiver has been determined to be unavailable, sending an alert message from the nurse call server to a portable communication device of the secondary caregiver to notify the secondary caregiver of any alert calls originating from any of the secondary caregiver's assigned patient rooms if the secondary caregiver has not been determined to be unavailable.

In some embodiments of the eighth aspect, if the secondary caregiver has also been determined to be unavailable, the method includes sending an alert message from the nurse call server to a portable communication device of a closest caregiver, other than the primary and secondary caregiver, as determined by the locating server to be closest to the patient room from which a respective alert call has originated if the closest caregiver has not been determined to be unavailable. If the closest caregiver has also been determined to be unavailable in the eighth aspect, the method may further include sending an alert message from the nurse call server to the portable communication device of a next closest caregiver, other than the primary and secondary caregiver, as determined by the locating server to be next closest to the patient room from which a respective alert call has originated if the next closest caregiver has not been determined to be unavailable.

Optionally, the method of the eighth aspect may include, with the nurse call server or the locating server, designating one or more caregivers as unavailable based on a qualification of the respective caregiver or the role of the respective caregiver. Alternatively or additionally, the method of the eighth aspect may include, with the nurse call server or the locating server, designating one or more caregivers as unavailable based on a distance between the respective caregiver and the patient room in which a respective alert call has originated exceeding a distance threshold.

In some embodiments of the method of the eighth aspect, the plurality of transceivers and the plurality of locating tags may communicate via ultra-wideband (UWB) signals. Furthermore, the location of the plurality of locating tags in the method of the eighth aspect may be determined by the locating server using two way ranging and/or time difference of arrival (TDOA) techniques. The locating server of the eighth aspect may use signals from only a subset of the plurality of transceivers to determine the location of each locating tag of the plurality of locating tags. The subset may be determined based on signal strength of UWB signals between the transceivers and the respective locating tag, for example. If desired, the subset may include at least three transceivers from the plurality of transceivers having highest signal strength values as compared to others of the plurality of transceivers.

If desired, the method of the eighth aspect may further include, with the nurse call server or locating server, designating one or more caregivers as unavailable if the caregivers are located in predetermined non-patient room areas of the healthcare facility. For example, the predetermined non-patient room areas of the hospital may include bathrooms.

Additional features, which alone or in combination with any other feature(s), such as those listed above and those listed in the claims, may comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying figures, in which.

DETAILED DESCRIPTION

Figure 1:
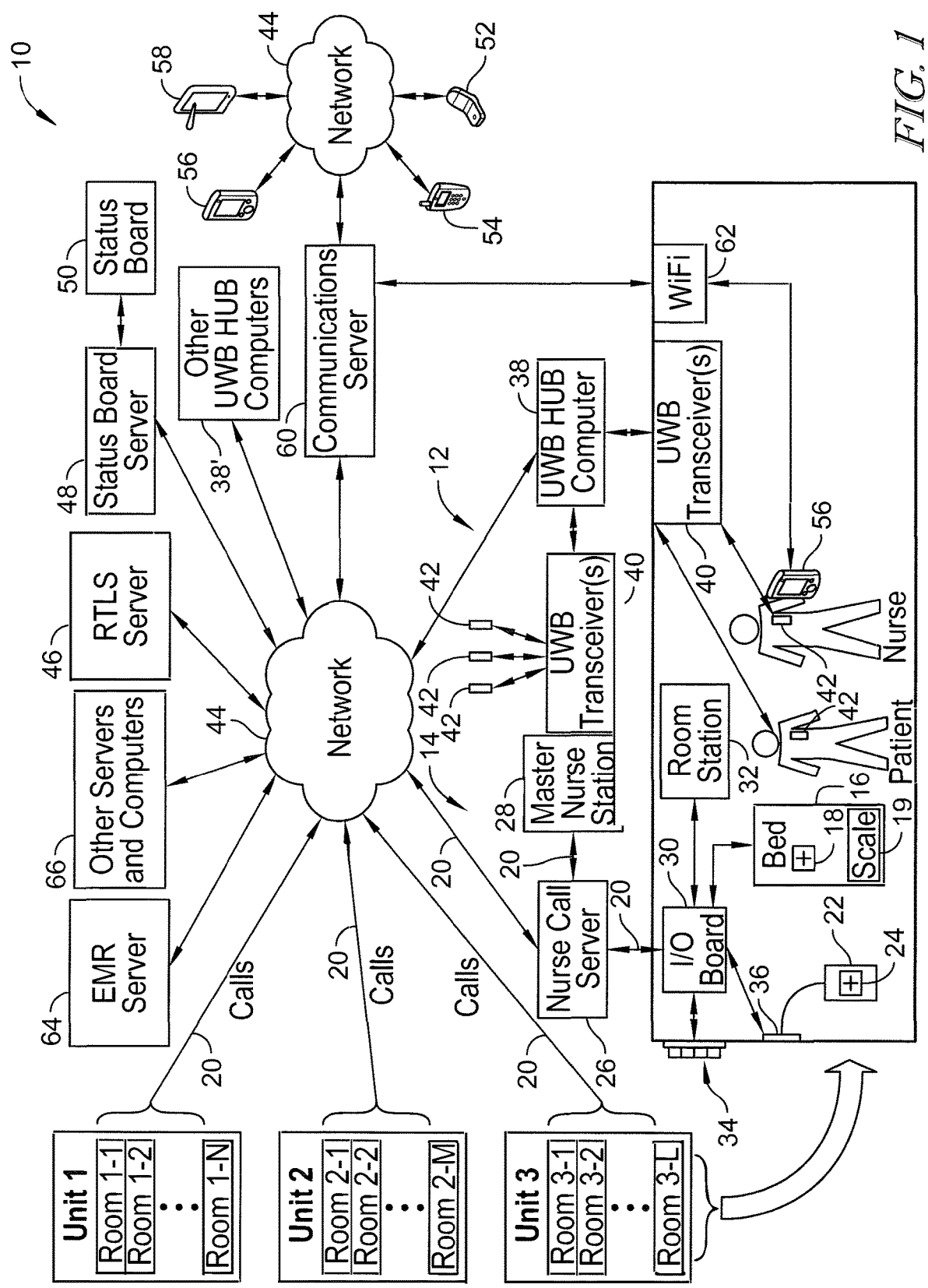
FIG. 1 is a block diagram of a healthcare information system for use in a healthcare facility having patient rooms in various units of the healthcare facility; the healthcare information system including various servers, nurse call equipment, and locating equipment that operate to determine caregiver availability to respond to nurse calls or requests from patients; the nurse call equipment including a nurse call server, a master nurse station coupled to the nurse call server, room stations located in the patient rooms, indicator assemblies located outside the patient rooms and coupled to the room stations via an input/output (I/O) board, and nurse call buttons on a patient bed and/or on a handheld pillow speaker unit; and the locating equipment including locating tags worn by caregivers and patients, ultra-wide band (UWB) transceivers located in the patient rooms, and an RTLS server coupled to the UWB receivers via an UWB hub computer or gateway.

According to the present disclosure, a healthcare information system 10 includes locating equipment 12 to track the whereabouts of caregivers in a healthcare facility and nurse call equipment 14 to receive nurse calls or other alerts from patients located in patient rooms of the healthcare facility as shown diagrammatically in FIG. 1. The healthcare facility is divided up into units as also shown diagrammatically in FIG. 1 as unit 1, unit 2, and unit 3. Units 1-3 each have patient rooms which, in the illustrative example, are shown as rooms 1-1 through 1-N for unit 1, rooms 2-1 through 2-M for unit 2, and rooms 3-1 through 3-L for unit 3. Letters N, M and L represent integers corresponding to the overall number of rooms in the corresponding units 1-3 and the use of different letters is intended to indicate that different units may not necessarily have the same number of rooms as other units.

The present disclosure is primarily directed to a system and method for determining which caregivers are unavailable and which caregivers are available to respond to the various alerts being communicated to nurse call system 14. The unavailability determination is made based on the locations of the caregivers within the healthcare facility as determined by locating equipment 12 along with other associated rules as will be discussed in further detail below in connection with FIGS. 2A and 2B. The rules for making the unavailable/available determination for each of the caregivers to respond to nurse calls and other alerts may vary from unit to unit in some embodiments.

While healthcare facilities may have any number of units with various unit names and all such facilities are intended to be within the scope of the present disclosure, examples of units of a healthcare facility may include, for example, a maternity unit, a pediatrics unit, an intensive care unit, and a med/surg unit, just to name a few. Each room of each unit typically has a patient support apparatus, such as a hospital bed 16 as shown in FIG. 1 in the enlarged diagrammatic view of one of the patient rooms. In some embodiments, bed 16 includes a nurse call button 18 that is pressed by a patient to send a nurse call to nurse call equipment 14 of system 10. The nurse call equipment 14 is sometimes referred to herein as nurse call system 14. Alternatively or additionally, some rooms may have a handheld pillow speaker unit 22 with its own nurse call button 24 as shown diagrammatically in FIG. 1. Nurse calls and other alerts, as discussed in further detail below, that originate from the various patient rooms of units 1-3 such as in response to buttons 18, 24 being pressed, are represented diagrammatically by arrows 20 in FIG. 1. Buttons 18, 24 and/or handheld pillow speaker unit 22 may be considered part of nurse call equipment 14 in some embodiments.

In the illustrative example, bed 16 includes a scale 19 to weigh a patient that is located on bed 16. Scale 19, in some embodiments, includes load cells as is well-known in the hospital bed art. In addition to weighing respective patients on beds 16, the load cells of scale 19 are used to monitor patient position on bed 16 and to monitor patient exit from bed 16. Thus, scale 19 in FIG. 1 also diagrammatically represents a bed exit and/or patient position monitoring (PPM) system of the respective bed 16. In response to a patient 16 being out of position on bed 16 or exiting bed 16 when the bed exit or PPM system is enabled, an alert is generated by the circuitry of bed 16 and is transmitted to the nurse call system 14. Additional details of scale 19 and bed exit and/or PPM systems, can be found in the following patent references, each of which is hereby incorporated by reference herein in its entirety to the extent not inconsistent with the present disclosure which shall control as to any inconsistencies: U.S. Pat. Nos. 9,358,168; 9,383,251; 9,009,893; 8,717,181; 8,598,893; 7,752,926; 7,464,605; 7,335,839; 7,253,366; 7,176,391; 6,924,441; 6,680,443; 6,208,250 and 6,067,019.

Other embodiments of bed exit and PPM systems contemplated by this disclosure employ the use of other patient presence/absence detection sensors in lieu of, or in addition to, load cells, such as, for example, resistive sensors including force sensitive resistors (FSR's), capacitive sensors, pressure sensors, piezoelectric patches or layers, optical sensors such as infrared sensors, cameras, and the like. Block 19 in FIG. 1 is intended, therefore, to diagrammatically represent all types of bed exit and/or PPM systems regardless of the type of sensor employed for detecting whether or not a patient is present on bed 16 and/or whether a patient on bed 16 is properly positioned or out of position on bed 16 in some respect.

According to the present disclosure, bed 16 is configured to generate many other alerts that are communicated to nurse call system 14. Examples of such additional alerts include siderail position alerts or siderail down alerts indicating that one or more siderails of bed 16 have been moved from a raised position to a lowered position, brake-not-set alerts indicating that one or more casters of bed 16 have been released or unbraked, bed height alerts or bed-not-low alerts indicating that an upper frame of bed 16 is no longer in its lowest position relative to a base frame of bed 16, head-of-bed (HOB) angle alerts indicating that a head section of a mattress support deck of bed 16 is lowered below a threshold angle (e.g., 30 degrees), mattress alerts relating to issues with mattress functions, and bed component temperature alerts indicating a high temperature condition of a respective bed component (e.g, actuator motor, air pump, electric circuit, etc.) just to name a few bed-generated alerts.

Some beds 16 contemplated by the present disclosure are equipped with one or more integrated heartrate (HR) and/or respiration rate (RR) sensors to monitor HR and/or RR, as the case may be. See, for example, U.S. Pat. Nos. 8,525,679 and 8,281,433, as well as U.S. Patent Application Publication No. 2018/0184984, each of which is hereby incorporated by reference herein in its entirety to the extent not inconsistent with the present disclosure which shall control as to any inconsistencies. Thus, in such embodiments, circuitry of bed 16 also sends alerts relating to HR and RR (e.g., HR too high or too low, RR too high or too low) to nurse call system 14.

It is also within the scope of the present disclosure for other patient care equipment, separate from bed 16, in patient rooms 1-1 through 3-L to send alerts to nurse call system 14. Examples of such other patient care equipment include physiological monitors such as heart rate monitors, respiration rate monitors, pulse oximeters, temperature monitors, blood pressure monitors, and so forth; other patient monitors such as electrocardiographs (EKG's), electroencephalographs (EEG's), capnographs, spirometers, and so forth; intravenous (IV) pumps, medication delivery pumps, ventilators, limb compression devices that treat deep vein thrombosis (DVT's) and the like. In some embodiments, alerts from such patient care equipment are provided to the nurse call system 14 via ports or jacks installed in the patient rooms and configured to mate with corresponding connectors at the ends of cables extending from the patient care equipment. See, for example, U.S. Pat. No. 9,411,934 which is hereby incorporated by reference herein in its entirety to the extent not inconsistent with the present disclosure which shall control as to any inconsistencies. In other embodiments, alerts from the patient care equipment are communicated to the nurse call system 14 wirelessly via wireless access points 62 and one or more communications servers 60 included in a network 44 of the healthcare facility. Separate call switches, such as pull cords in a bathroom adjacent the patient rooms, also generate alerts that are communicated to the nurse call system 14 according to the present disclosure.

Based on the foregoing, it should be appreciated that beds 16, pillow speaker units 22, the other patient care equipment, and the call switches discussed above, are examples of alert placement devices according to the present disclosure. Other examples of alert placement devices are provided below. Thus, the term alert placement device is intended to broadly cover any device that communicates an alert to nurse call system 14 and to which a caregiver is to respond. As noted above, the present disclosure is primarily directed to a system and method for determining which caregivers are unavailable and which caregivers are available to respond to the various alerts being communicated to nurse call system 14 by the alert placement devices.

Nurse call equipment 14 includes a nurse call server 26 and a master nurse station 28 as shown diagrammatically in FIG. 1. It should be appreciated that some healthcare facilities may have two or more servers 26 and two or more master nurse stations 28. For example, a master nurse station may be provided for each unit of the healthcare facility, if desired. In the illustrative example, nurse call equipment 14 also includes, in each room, an input/output (I/O) board 30 (sometimes referred to as a room control board (RCB)) that receives nurse call signals from the one or more beds 16, pillow speaker units 22, and other patient care equipment in the room. Nurse call equipment 14 also includes at least one room station 32 in each room and at least one indicator assembly 34 (sometimes referred to as a dome light assembly or just a dome light) located in a hallway adjacent to the room. Such dome lings 32 are sometimes located above doorways to the respective patient rooms.

In some embodiments, room stations 32 include a code blue lever that is actuated by a caregiver to send an alert signal to server 26 in response to the patient in the respective room going into cardiac arrest. Some room stations 32 also include a caregiver input that can be actuated or selected to place an assist call to summon other caregivers to the room for assistance. Thus, room stations 32 are another example of alert placement devices according to the present disclosure. Each I/O board 30 is communicatively coupled to a respective server 26, room station 32, and indicator assembly 34. In the illustrative example, a wall connector 36 is provided for coupling to a cable extending from unit 22 and the connector 36 is coupled to I/O board 30.

I/O board 30 passes any nurse calls 20 made by a patient using button 18 of bed 16 or button 24 of unit 22 to server 26. Information concerning the nurse calls and other alerts 20 made in the various rooms is displayed on display screens, such as graphical user interfaces (GUI's), of room stations 32 and master nurse station 28. In some embodiments, additional components are included in nurse call equipment 14 such as, for example, bed interface units (BIU's), routers, gateways, cabling, etc. One example of nurse call equipment 14 contemplated by the present disclosure is the NAVICARE® nurse call system available from Hill-Rom Company, Inc. Additional details of suitable nurse call equipment 14 that may be included in system 10 are shown and described in U.S. Pat. Nos. 8,598,995; 8,384,526; 8,169,304; 8,046,625 and 7,319,386; each of which is hereby incorporated by reference herein to the extent not inconsistent with the present disclosure which shall control as to any inconsistencies.

Still referring to FIG. 1, locating equipment 12 includes a real-time locating system (RTLS) server 46, a multitude of RTLS receivers 40 located throughout the healthcare facility, and a multitude of RTLS badges or tags 42 that are worn by caregivers, such as by being clipped to the caregiver's clothing for example. As the caregivers travel throughout the healthcare facility, tags 42 transmit signals to the receivers 40 at the caregiver's location. The signals from tags 42 each include a unique tag identification code or number (ID) that is correlated in a database of server 46 to the identity of the caregiver to which the particular tag 42 has been assigned. In some embodiments, patients also wear tags 42 so that locating equipment 12 operates to track the whereabouts of patients throughout the healthcare facility as well. Such patient tags 42 may be included in wristbands worn by the patients or may be clipped to the gown or clothing of the patients.

Receivers 40 each transmit to server 46 a receiver ID along with the tag ID of any tags 42 within the reception range of the particular receiver 40. The receiver ID is correlated in the database of server 46 to a particular location, such as a room or hallway, of the healthcare facility. Thus, based on the transmissions from the various receivers 40 of receiver ID and tag ID, server 46 determines the location of each of the caregivers, and if applicable, the patients, having an associated tag 42 within the healthcare facility. Tags 42 may be attached to particular pieces of equipment (e.g., beds, wheelchairs, IV pumps, vital signs monitors, etc.) so that locating equipment 12 is able to track the locations of the equipment in a similar manner, if desired.

It is within the scope of the present disclosure for locating equipment 12 to implement any of a variety of wireless communication technologies to achieve the function of tracking the whereabouts of caregivers in a healthcare facility. Radio frequency (RF) including WiFi (i.e., 802.11) or Bluetooth (BT), infrared (IR), ultrasonic (US), ultra wide band (UWB), and so forth are a few examples of such technologies. In some embodiments, for example, locating units (not shown) mounted throughout the healthcare facility transmit IR signals to tags 42. The IR signals are encoded with a location ID which correlates in the database of server 46 to the location of the locating unit. The tags 42 then transmit the location ID's and tag ID's as an RF signal to receivers 40. Thus, tags 42 in such embodiments have an IR receiver and an RF transmitter. The receivers 40 transmit the location ID's (sent originally via IR) and the tag ID's to server 46 for correlation. Thus, receivers 40 may be more accurately characterized as receiver/transmitters or transceivers in some embodiments since they both transmit and receive. Such a system that uses IR and RF technology for locating is marketed, for example, by Centrak Inc. of Newtown, Pa.

Nurse call equipment 14 and locating equipment 12 are communicatively coupled to one another by a healthcare information system (HIS) network 44 which is illustrated diagrammatically in FIG. 1 but which is intended to represent all of the infrastructure of a healthcare facility, such as gateways, routers, cabling, network servers, and the like, used to interconnect computer devices including various servers, such as servers 26, 46, in a healthcare facility. In this regard, nurse call server 26 of nurse call equipment 14 receives information from RTLS server 46 of locating equipment 12 regarding the location of various caregivers having tags 42, as they travel throughout the healthcare facility.

According to this disclosure, each time a patient places a nurse call 20, nurse call server 26 keeps track of the amount of time that elapses subsequent to the respective nurse call 20 being placed. Thus, each nurse call 20 has a timer associated therewith which is implemented in nurse call software executed by server 26. When a caregiver wearing one of tags 42 enters a particular room having an outstanding nurse call 20, nurse call server 26 stops the timer of the nurse call 20 for that particular room, either substantially in real time upon entry of the caregiver into the room or after a threshold amount of the caregiver's presence in the room, such as one to five minutes, for example. As such, nurse call server 26 is able to keep track of nurse call response times for each nurse call 20. Server 26 also has data concerning the overall total number of nurse calls at any given time. Data from server 38 also indicates how long each caregiver having a respective tag 42 is present in each patient room.

In some embodiments, server 26 also provides to the RTLS server 46 information concerning which unit (e.g., units 1-3) each of the calls originated. According to this disclosure, the rules for determining caregiver availability and unavailability vary by unit as noted above. Thus, based on information from server 26, server 46 is able to determine which availability/unavailability algorithm to execute for each of the incoming alert calls 20. In some embodiments, server 26 executes the availability/unavailability algorithm in lieu of server 46.

In some scenarios contemplated by this disclosure, patient's have their own tablets or smart phones on which communication software is installed for interfacing with system 10 via network 44. Alternatively or additionally, a healthcare facility may provide the patient with a tablet or other digital device for use during their stay at the facility. Various call type icons are displayed on the GUI of the patient's personal digital device in connection with the communication software. Selection of a call type icon on the patient's GUI results in a nurse call 20 being sent to server 26 with information concerning the call type. In this regard, see, for example, U.S. Patent Application Publication No. 2016/0055299 which is hereby incorporated by reference herein to the extent not inconsistent with the present disclosure which shall control as to any inconsistencies. Such patient tablets or digital devices that are capable of placing nurse calls are also within the scope of the term alert placement devices according to this disclosure. Beds 16 with patient GUI's for placing specific call types are also contemplated by this disclosure and are within the scope of term alert placement devices. See, for example, U.S. Pat. No. 9,286,441 which is hereby incorporated by reference herein to the extent not inconsistent with the present disclosure which shall control as to any inconsistencies.

It is also contemplated by this disclosure that a variety of different types of alerts and notifications can be initiated by the server 26. For example, when a nurse call 20 is placed by a patient in a particular room, one of the lights of indicator assembly 34 associated with the room becomes illuminated in a first state, such as for example, a non-flashing amber or yellow light. In some embodiments, if the nurse call 20 is not answered by a caregiver visiting the patient room within a first threshold amount of time, the patient experience module signals the particular indicator assembly 34 via server 26 and I/O board 30 to cause the yellow light to flash on and off. If the nurse call 20 is not answered by a caregiver visiting the patient room within a second threshold amount of time, the patient experience module signals the indicator assembly 34 via server 26 and I/O board 30 to illuminate a red light and to turn off the flashing yellow light. In some embodiments, if a caregiver at master nurse station 28 opens up a communication channel to speak with the patient placing the nurse call, then server 26 signals indicator assembly 34 via I/O board 30 to illuminate a green light. Thus, the lights of indicator assemblies 34 serve as one type of alert or notification to caregivers as to the status of the associated nurse calls 20 and whether nurse calls 20 are being answered by caregivers with visits to the patient rooms within acceptable time thresholds.

Some or all of the various alert calls 20 occurring within system 10 are shown on display screens of various computer devices in some embodiments. For example, server 26 sends a message or information regarding text and/or an icon to be displayed on the GUI of master nurse station 28 relating to each of the active alert calls. In some embodiments, system 10 includes a status board server 48 which communicates with servers 26, 46 via network 44. One or more status boards 50 are coupled to server 48. Server 26, therefore, communicates messages or information to server 48 to cause text and/or icons to be displayed on the status board 50 in connection with the various alert calls 20. Status board 50 typically includes a display screen that is much larger than a display screen of a regular computer or master nurse station 28. The status board 50 is usually mounted in an area that is highly trafficked by caregivers so as to be readily visible by caregivers during their shifts. For additional details of a suitable status board 50, see U.S. Pat. No. 8,779,924 which is hereby incorporated by reference herein to the extent not inconsistent with the present disclosure which shall control as to any inconsistencies.

Further according to this disclosure, computer devices that receive messages or notifications relating to the various alert calls 20 include wireless communication devices carried by caregivers. As shown in FIG. 1, such wireless communication devices include, for example, telephone handsets 52, pagers 54, smart phones 56, and tablet computers 58. Each of these wireless devices 52, 54, 56, 58 have a display screen on which the message and/or information about alert calls 20 pertaining to the respective caregiver is displayed. One or more communications servers 60 are provided in system 10 in the illustrative example to facilitate the communication of such alerts or notifications from one or more of servers 26, 46 to devices 52, 54, 56, 58. One or more of servers 60 may be a voice over Internet Protocol (VoIP) server in some embodiments.

As shown in FIG. 1, system 10 includes other communication infrastructure, such as wireless access points (WAP's) 62 that are communicatively coupled to server 60 and that are mounted throughout the healthcare facility. WAP's communicate with the various wireless communication devices 52, 54, 56, 58 carried by caregivers and also communicate with digital devices, such as tablet computers, that are used by patients. In some embodiments, in which tags 42 communicate via WiFi signals, WAP's are used as part of locating system 12 in addition to, or in lieu of, receivers 40. Thus, in some embodiments, WAP's communicate information from tags 42 to server 46 via server 60 and other infrastructure of network 44.

As also shown in FIG. 1, an electronic medical record (EMR) server 64 and other servers and computers 66 are also included in system 10 and are coupled to the network 44 of the healthcare facility. The various alert calls 20 and information about caregiver responses to such alert calls 20 are logged in EMR server 64 in some embodiments. The other servers and computers 66 may include, for example, admission/discharge/tracking (ADT) servers and computers that are used for assigning incoming patients to patient rooms, for tracking any changes to the room assignments, and for discharging outgoing patients.

As noted above, the locating equipment 12 in some embodiments is embodied as an ultra-wideband (UWB) locating system 12, which according to this disclosure is considered to be a high-accuracy locating system. In such embodiments, tags 42 are configured as UWB tags 42 having UWB transceivers, and transceivers 40 are configured as UWB transceivers. The UWB transceivers 40 are stationary and the UWB transceivers of tags 42 are mobile, but their circuitry otherwise may be substantially the same as that of transceivers 40. Thus, tags 42 and transceivers 40 each include a housing that contains associated circuitry. The circuitry of tags 42 and transceivers 40 includes, for example, a processor such as a microprocessor or microcontroller or the like, memory for storing software, and communications circuitry including a transmitter, a receiver and at least one antenna. Transceivers 40 each include mounting hardware, such as brackets or plates or the like, in some embodiments, to permit the transceivers 40 to be mounted at fixed locations in the patient rooms and other locations of the healthcare facility with fasteners such as screws or the like.

In the illustrative example of system 10 of FIG. 1, the high-accuracy locating system 12 further includes an UWB hub computer 38 which is communicatively coupled to other UWB hub computers 38' of the high-accuracy locating system 12 via network 44 of the healthcare facility. UWB hub computer 38 serves as an intermediary between transceivers 40 and RTLS server 46. Of course, the other UWB hub computers 38' are also communicatively coupled to respective sets of transceivers 40 and to server 46. In the illustrative example, the high-accuracy locating system 12 is also communicatively coupled to other servers or computers 66 of the healthcare facility, as well as to nurse call server 26 and EMR server 64, just to name a few.

As shown diagrammatically in FIG. 1, various lines interconnect transceivers 40 with hub computer 38 and interconnect servers and computers 26, 28, 46, 48, 60, 64, 66 with each other via network 44. It should be appreciated that these lines represent bidirectional communication over wired data links (including electrical wires or fiber optic data links) and/or wireless data links, at the discretion of the designer of system 10. UWB transceivers 40 communicate wirelessly with tags 42 using radio frequency (RF). It is known that RF signals are able to pass through walls, ceilings, floors, and other objects such as people and equipment. Thus, according to this disclosure, it is not required that each patient room has a transceiver 40 located therein in those embodiments of the locating system 12 using RF communication.

According to this disclosure, the portion of system 10 that operates as a high-accuracy locating system 12 using UWB technology is able to determine the location of each tag 42 that is in communication with at least three of transceivers 40 within about one foot (30.48 cm) or less of the tag's actual location. In other embodiments, the locating system 12 is able to determine the location of each tag 42 that is in communication with at least three of transceivers 40 within about three feet (91.44 cm) or less of the tag's actual location and such embodiments are still considered to be high-accuracy locating systems 12 according to the present disclosure. When the term "about" is used in the present disclosure in connection with a numerical value, it is intended to mean within plus or minus 10% of the recited value.

In some embodiments, the high-accuracy locating system 12 is operable to determine the location of tags 42 in 3-dimensional space. However, in many embodiments, it suffices to determine the location of tags 42 in 2-dimensional space. Accordingly, X and Y directions relative to a floor plan of the healthcare facility are established by software residing in server 46 and/or hub computers 38, 38' with a designated point on the floor plan, such as a corner of one of the patient rooms of each of units 1-3, serving as an arbitrary origin of an X-Y coordinate system of the respective unit. The Z dimension corresponds to a height in a Z direction (not shown) above the floor plan. UWB locating systems typically operate within the 3.1 gigahertz (GHz) to 10.6 GHz frequency range. Suitable transceivers 40 in this regard include WISER Mesh Antenna Nodes and suitable tags 40 in this regard include Mini tracker tags, all of which are available from Wiser Systems, Inc. of Raleigh, N.C. and marketed as the WISER LOCATOR™ system.

In some embodiments, the high-accuracy locating system 12 implementing UWB technology uses 2-way ranging, clock synchronization, and time difference of arrival (TDOA) techniques to determine the locations of tags 42 in the X and Y directions (and, optionally, the Z direction in some embodiments). See, for example, International Publication No. WO 2017/083353 A1, which is hereby incorporated by reference herein in its entirety for all that it teaches to the extent not inconsistent with the present disclosure which shall control as to any inconsistencies, for a detailed discussion of the use of these techniques in a UWB locating system. Using these techniques, distances between the stationary transceivers 40 and the various mobile tags 42 are determined based on bidirectional wireless signals communicated between tags 42 and transceivers 40. For example, the distance from each transceiver 40 to any particular tag 42 can be resolved onto the X-Y plane as a circle having a radius equal to the distance and having its center at the particular transceiver 40. The actual location of the mobile tag 42 is determined based on the point of intersection of three or more of the circles defined by radii from three or more corresponding transceivers 40.

The location of each stationary transceiver 40 is mapped onto the X-Y coordinate system by server 46 in some embodiments. Thus, each transceiver 40 has its own X and Y coordinates relative to the designated arbitrary origin. As the mobile tags 42 move throughout the healthcare facility, server 46 determines the X and Y coordinates of the various mobile tags 42 relative to the origin based on the distances from the known X and Y coordinates of the transceivers 40.

It should be appreciated that, unless a tag 42 is midway between two transceivers 40 on a straight line connecting the two transceivers 40 (in which case the two circles generated will be tangent to each other at a single point), then two circles that are generated from the two transceivers 40 will intersect at two points such that a circle generated from a third transceiver 40 is needed to determine which of the two points is the one corresponding to the location of the tag 42. Generating fourth, fifth, sixth, etc. circles having other transceivers 40 as their respective centers will further increase the accuracy of determining the actual location of the particular tag 42. Due to small errors introduced by refraction of the RF signal through solid objects, including walls, people, equipment, etc., the three or more circles in many instances will not intersect at exactly the same point and so interpolation between clusters of circle intersections is performed to arrive at the calculated location of the particular mobile tag 42 of interest on the X-Y plane. These considerations are discussed in International Publication No. WO 2017/083353 A1 which is already incorporated by reference herein.

Tracking the locations of multiple mobile tags 42 in substantially real time using 2-way ranging, clock synchronization, TDOA, resolution of circles onto the X-Y plane, and interpolating intersection point clusters of the circles requires a large amount of computational power by hub computers 38, 38' and/or the associated RTLS server 46. Thus, each hub computer 38, 38' of the high-accuracy locating system 12 receives incoming data from a predetermined number of transceivers 40. TDC Acquisition Holdings, Inc. of Huntsville, Ala. which does business as Time Domain, makes a hub computer (referred to as the PLUS Synchronization Distribution Panel) that is capable of receiving incoming data from up to 144 transceivers. The locating server 46, in turn, receives data from the various hubs 38, 38' and tracks or monitors the locations of tags 42 in the healthcare facility.

Regardless of the number of transceivers 40 coupled to hub computers 38, 38', it is contemplated by the present disclosure that, in some embodiments, locating server 46 and/or hub computers 38, 38' are programmed to use signals from only a subset of the plurality of transceivers 40 to determine the location of any given locating tag 42. For example, the subset may be determined based on signal strength of signals between the particular locating tag 42 and the plurality of transceivers 40. The subset may include at least three transceivers 40 from the plurality of transceivers 40 having highest signal strength values as compared to others of the plurality of transceivers 40.

Figure 2A:
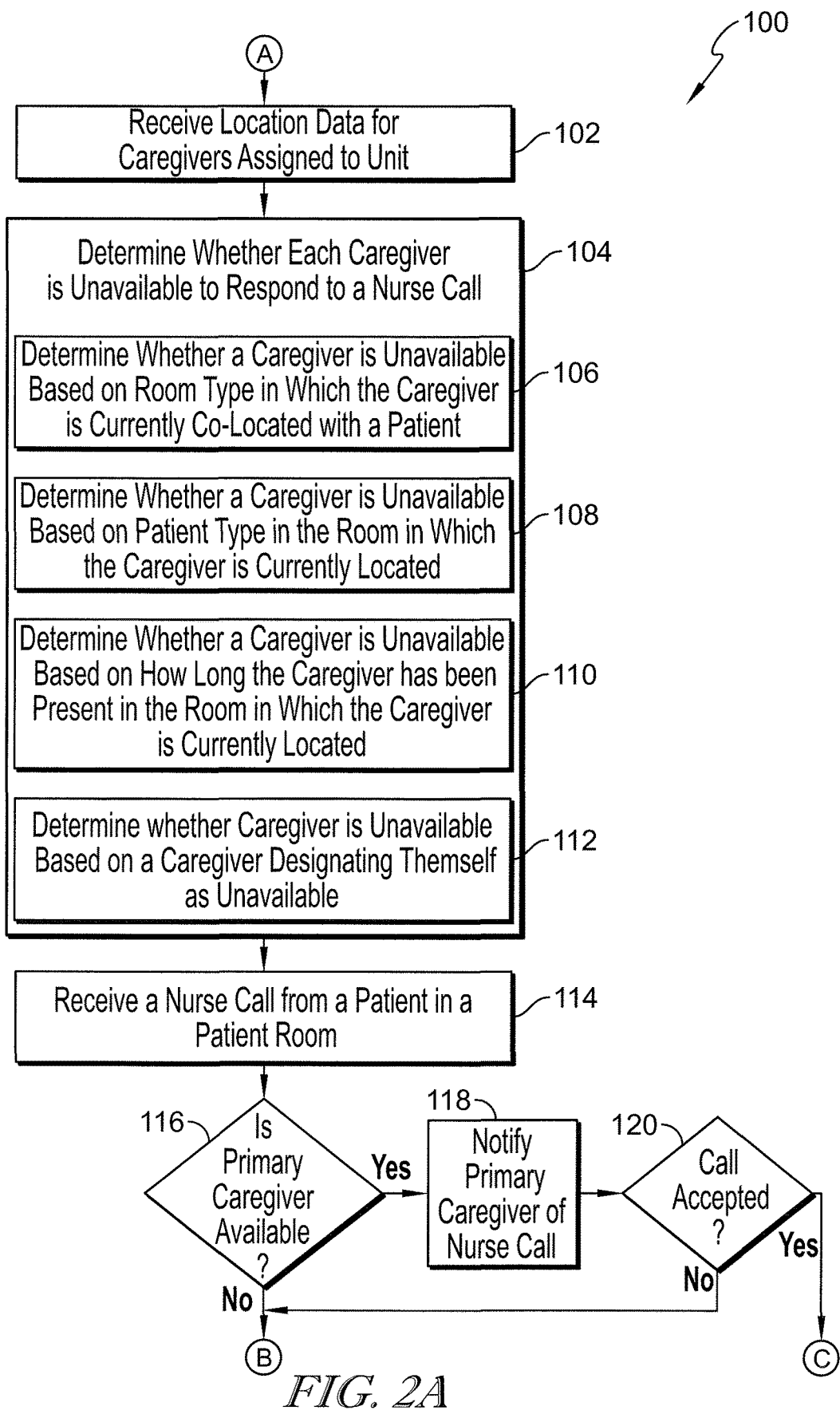
FIGS. 2A and 2b together form a flow diagram of at least one embodiment of a method for determining caregiver availability to respond to patient calls or requests.
Figure 2B:
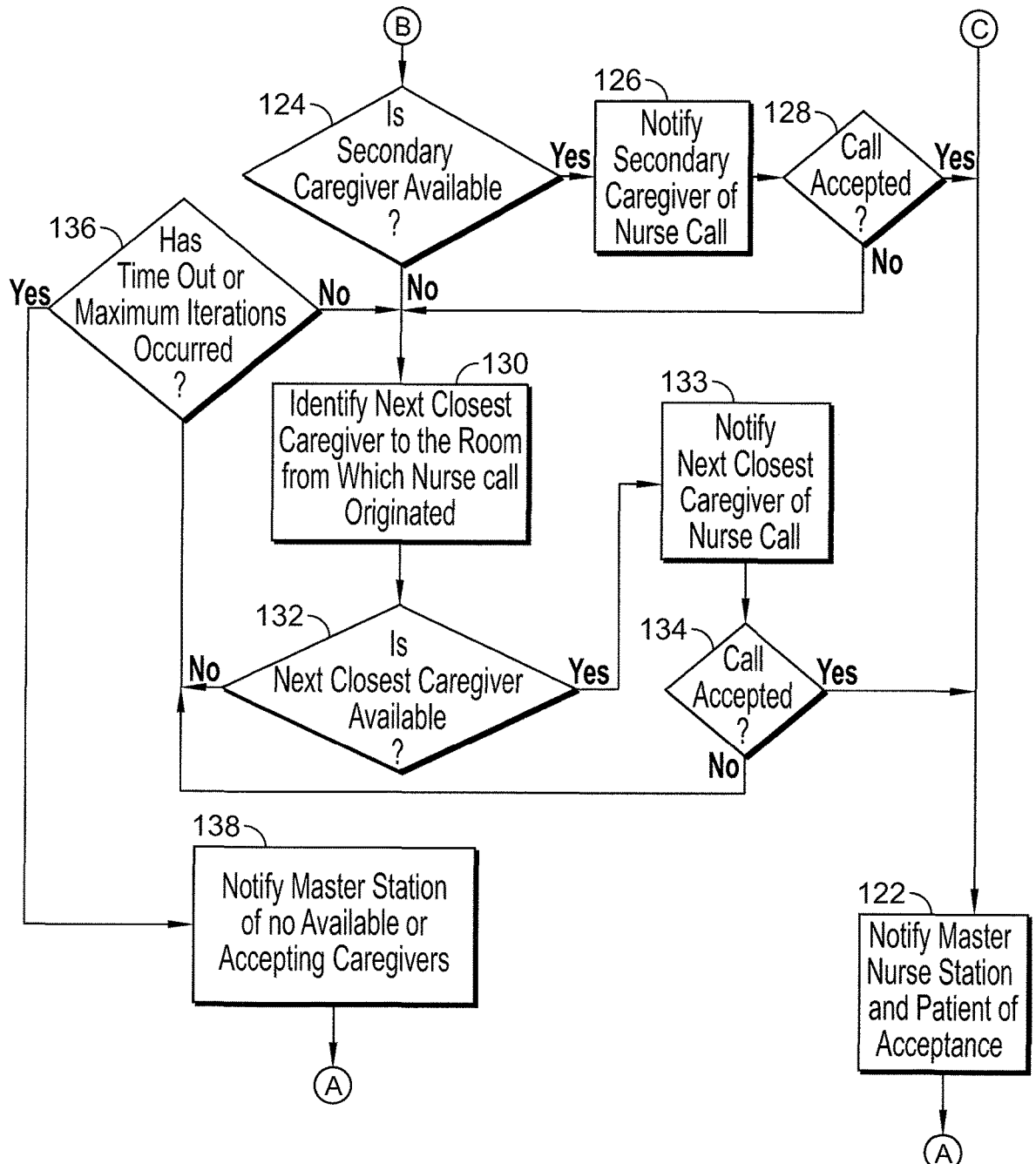

Referring now to FIGS. 2A and 2B, an example of a caregiver unavailability determination algorithm 100 contemplated by the present disclosure is provided and may be implemented as software executed by server 26 and/or server 46. Thus, in some embodiments, algorithm 100 may be performed entirely by server 26 (based on relevant information received from server 46), entirely by server 46 (based on relevant information received from server 26), or with each of servers 26, 46 performing designated portions of the algorithm 100. The algorithm 100 begins at block 102 in which location data is received for the caregivers assigned to a particular unit. Thus, block 102 corresponds to the locating system 12 detecting current locations of caregiver tracking tags 42 within the healthcare facility. Algorithm 100 then proceeds to block 104 at which a determination is made for each caregiver as to whether the caregiver is available or unavailable to respond to alert calls.

Within block 104 of FIG. 2A are sub-blocks that each correspond to various rules for caregiver unavailability determination. At sub-block 106, the rule for determining caregiver unavailability is made based on a room type in which the caregiver is currently co-located with a patient. For example, if the caregiver is currently determined to be in an operating room, therapy room or a bathroom based on the location of the caregiver tracking tag 42, as determined by locating system 12, at the same time a patient is also located in the same room, the identified caregiver is considered to be unavailable to respond to alert calls originating in other rooms. In such embodiments, the caregiver is not designated as unavailable if they are in an operating room, therapy room, or bathroom without a patient also being present. Thus, if the caregiver is in a designated type of room without a patient also being present, according to the rule of sub-block 106, then the caregiver is still considered to be available for responding to alert calls. This is an improvement over the system disclosed in U.S. Pat. No. 9,652,960 in which the unavailability determination is made based only on the type of room in which the caregiver is currently located without regard to whether or not a patient is also present.

As noted above, patient presence in a particular room may be made via detection by locating system of a tag 42 assigned to a patient in the particular room, or via detection by bed exit/PPM system 19 that a patient is present on the respective patient support apparatus 16 in the particular room. All variants of locating equipment 12 and/or system 19, therefore, are considered to be patient detectors according to the present disclosure. In some embodiments in which RTLS 12 is a high-accuracy locating system 12, caregivers are determined to be unavailable according to the rules of sub-block 106 only if they are within a threshold distance of the patient within a particular room or within a predetermined distance of patient bed 16 within the patient room. The assumption under such a scenario is that the caregiver is not attending to the patient present in the patient room so as to be designated unavailable, unless the caregiver is relatively close to the patient (e.g., about three to about five feet or less).

It should be appreciated that the examples of an operating room, a therapy room, and bathroom as being the room type set forth in sub-block 106 for determining caregiver unavailability are given as arbitrary examples. The room types for determining caregiver unavailability when the caregiver is co-located with a patient according to the rule of sub-block 106 are at the discretion of the system programmer and may include any desired room type of a healthcare facility. Furthermore, a hallway is also considered to be within the scope of a designated room type of the rule of sub-block 106 in some embodiments. For example, if locating system 12 is a high-accuracy location system 12, such as one employing UWB technology, then the presence of a patient tag 42 within a threshold distance of the caregiver tag 42 in a hallway, such as within about 1 to about 4 feet (30.5 cm to 121.9 cm), results in the caregiver being designated as unavailable according to the rule of sub-block 106. In such a scenario, the assumption is that the caregiver is assisting the patient in walking down the hallway or is transporting the patient down the hallway such as in a wheelchair, for example. In either case, the caregiver is considered to be unavailable for responding to alert calls while attending to a patient in this manner.

At sub-block 108 within block 104 of FIG. 2A, the rule for determining caregiver unavailability is made based on a patient type in the room in which the caregiver is currently located. For example, if a patient is a critical care patient or one with a particular condition, such as having methicillin-resistant *Staphylococcus aureus* (MRSA), then the caregiver is designated as unavailable. For critical care patients, the assumption is that the caregiver needs extra time with the patient such as to change a wound dressing, replace a soiled incontinence detection pad or diaper, attended to adjustments of ventilators of intubated patients, and the like.

For MRSA patients and other patients requiring isolation procedures to be followed such as those producing airborne contaminants or having blood borne contaminants, caregivers are sometimes considered contaminated once entering the patient's room and therefore, may be required to go through a decontamination procedure after leaving the patient's room. For example, after entering the room of a contaminated patient, the caregiver is considered to be unavailable while in the patient room and for some period of time thereafter (e.g., ten minutes to an hour) for the performance of the decontamination process. The decontamination process can include, for example, removal and/or disposal of hazmat suits, clothes, gowns, gloves, face shields, and the like, as well as disposal of medical waste such as wound dressings and special handling of other medical items such as patient linens, IV pumps, and the like that have been removed from the contaminated patient's room. Thus, a timer is used during the implementation of the rule of sub-block 108 to determine the period of time that the respective caregivers are considered to be unavailable according to the rules of sub-block 108.

At sub-block 110 within block 104 of FIG. 2A, the rule for determining caregiver unavailability is made based on how long each caregiver has been present in a particular room in which the caregiver is located. For example, if a caregiver enters a room, such as one of patient rooms 1-1 through 3-L, and stays for a threshold period of time (e.g., five to ten minutes), then the caregiver is designated as unavailable. Thus, prior to the threshold period of time elapsing while the caregiver is in the particular room, the caregiver is still considered to be available. After the threshold period of time elapses, the caregiver is then designated as unavailable. The reasoning for the unavailability rule of sub-block 110 is that caregivers sometimes make routine, short checks of patients or visits to patients during their rounds, for example. These sorts of routine rounds oftentimes are not precipitated by alert calls 20. Thus, the caregivers are still considered to available to response to incoming alert calls for other patients. After a threshold period or amount of time, however, the assumption is that the caregiver is performing a more complex, time-consuming activity with, or on behalf of, the patient. Similar to rule 108, therefore, a timer is used during the implementation of the rule of sub-block 110 to determine when a caregiver's designation transitions from available to unavailable.

The server or servers, such as servers 26, 46, executing algorithm 100 implement the sub-block 108, 110 timers associated with the various caregivers in software, for example, in some embodiments. For example, a time at which a particular caregiver exits a room, in the case of the rule of sub-block 108, or enters a room, in the case of the rule of sub-block 110, is stored in memory and then compared to a current time as algorithm 100 runs. The comparison is used to determine a total time after room exit, or a total time after room entry, as the case may be, and then the total time is compared to the relevant threshold time. In the case of sub-block 108, after the total time exceeds the relevant threshold, the respective caregiver's designation switches from unavailable to available under the assumption that the caregiver has had time to decontaminate or otherwise complete the isolation protocols. In the case of sub-block 110, after the total time exceeds the relevant threshold, the respective caregiver's designation switches from available to unavailable under the assumption that the caregiver is performing an activity with the patient, or on behalf of the patient, that requires more time.

In the discussion above of sub-block 110, the example given is that of a caregiver entering a patient room, such as one of illustrative rooms 1-1 through 3-L. However, the rule of sub-block 110 can be implemented in connection with any type of room of a healthcare facility, including those that don't contain a patient, at the discretion of the system programmer. For example, if a caregiver enters a supply closet and remains in the supply closet beyond a threshold period of time, the caregiver may be designated as unavailable. Similarly, if the caregiver enters a supervisor's office, the caregiver may be designated as unavailable after a threshold period of time. As another example, if the caregiver enters a cafeteria of the healthcare facility, the caregiver may be designated as unavailable after a threshold period of time. These are given as just a few additional examples of ways in which the rule of sub-block 110 may be implemented in practice.

At sub-block 112 within block 104 of FIG. 2A, the rule for determining caregiver unavailability is made based on a particular caregiver designating himself or herself as unavailable. As noted above, caregivers sometimes carry one or more wireless communication device such as one or more of devices 52, 54, 56, 58. In some embodiments, software loaded on the wireless communication device 52, 54, 56, 58 carried by the caregiver renders one or more user inputs on the display screens of the respective device 52, 54, 56, 58 carried by the caregiver that are selectable by the caregiver to designated themselves as unavailable or available. In this regard, see U.S. application Ser. No. 16/143, 971, which is titled "Caregiver and Staff Information System," which was filed Sep. 27, 2018, which published as U.S. Patent Application Publication No. 2019/0108908 A1, and which is hereby incorporated by reference herein in its entirety to the extent not inconsistent with the present disclosure which shall control as to any inconsistencies, and particularly with reference to FIGS. 23, 24, and 50-52 and the related descriptions of those Figs. in the specification. Alternatively or additionally, such user inputs for caregivers to designate themselves as available or unavailable are displayed on graphical user interfaces (GUI's) or display screens of room stations 32 and/or beds 16 in some embodiments. If a caregiver designates himself or herself as unavailable, a timer is implemented in some embodiments so that the caregiver automatically reverts to being designated as available after a threshold amount of time expires or is reached. The threshold amount of time is selectable by the caregivers in some embodiments. The above discussion regarding the software implementation of a timer in connection with sub-blocks 108, 110 is equally applicable to sub-block 112.

According to embodiments contemplated by this disclosure, algorithm 100 is configured such that the rules of one, two, three, or four of sub-blocks 106, 108, 110, 112 of block 104 are implemented. That is, the rules of sub-blocks 106, 108, 110, 112 are not mutually exclusive. Furthermore, the rules of sub-blocks 106, 108, 110, 112 that pertain to Unit 1 of system 10 are different than those that pertain to Unit 2 which, in turn, are different than those that pertain to Unit 3, for example. If desired, however, the rules of sub-blocks 106, 108, 110, 112 that pertain to two or three of Units 1-3, for example, are the same in some embodiments. Even within the same Unit 1-3, the rules of sub-blocks 106, 108, 110, 112 are applicable to different rooms within the Unit in different combinations, if desired. Thus, all permutations and combinations of the rules of sub-blocks 106, 108, 110, 112, as well as the variants of each of these as discussed above, are within the scope of the present disclosure for inclusion in algorithm 100.

According to the illustrative algorithm 100, after determining whether each caregiver is unavailable to respond to an alert call 20 at block 104, based on the applicable rules of one or more of sub-blocks 106, 108, 110, 112 that are established at the option of the system programmer, a nurse call 20 from a patient of a patient room 1-1 through 3-L is received by nurse call system 14 as indicated at block 116 of FIG. 2A. Block 114 is also illustrative of receiving other types of alert calls 20 that originate from other pieces of patient care equipment as discussed above in connection with the examples of alert placement devices contemplated by the present disclosure. Thus, while the discussion of algorithm 100 that follows will refer to the alert call 20 received by algorithm 100 as a "nurse call 20" for the sake of illustration, it should be appreciated that the discussion is equally applicable to any type of alert call 20 generated within system 10 as discussed above.

After receiving the nurse call 20 at block 114, algorithm 100 proceeds to block 116 to determine whether a primary caregiver is available. For each patient in the patient rooms 1-1 through 3-L of Units 1-3, a primary caregiver and a secondary caregiver is typically assigned within the nurse call system 14 using master nurse station computer 28 or using some other administration computer of system 10. At block 116, if algorithm 100 determines that the primary caregiver is available (e.g., the primary caregiver has not been determined to be unavailable at block 104), algorithm 100 proceeds to send a message to notify the primary caregiver of the nurse call 20, as indicated at block 118 of FIG. 2A. As noted above, such notifications of nurse calls 20 may appear on the screens of one or more of room stations 32, master station 28, status board 50, and/or wireless communication devices 52, 54, 56, 58 carried by the primary caregiver. In this regard, the notification of nurse call 20 may appear on the room station 32 where the primary caregiver is determined to be located by the RTLS 12 in some embodiments.

After the primary caregiver has been notified of the nurse call 20 at block 118 because of their availability as determined at block 116, algorithm 100 proceeds to block 120 and determines whether the nurse call 20 has been accepted by the primary caregiver. Acceptance of the nurse call 20 by the primary caregiver indicates that the primary caregiver will respond to the particular nurse call 20, typically by going to the patient room from which the nurse call 20 originated or by calling the room using a nearby room station 32 or master station 28 or by using the wireless communication device 52, 54, 56, 58 carried by the caregiver. Algorithm 100 implements a timer in connection with block 120 to give the primary caregiver a threshold amount of time, such as on the order of about two to about ten minutes, to accept the nurse call 20. The discussion above of software implementation of timers is equally applicable to block 120.

If at block 120 of algorithm 100 the primary caregiver accepts the nurse call 20 within the relevant threshold amount of time, algorithm 100 proceeds to block 122, shown in FIG. 2B, to notify the master nurse station 28 and the patient of the acceptance of the nurse call 20. In a variant embodiment, the master nurse station 28 is notified of the primary caregiver's acceptance of the nurse call 20, but the patient is not notified. If the acceptance by the primary caregiver is made using one of devices 52, 54, 56, 58, the notification to the master station 38 of the acceptance is routed through network 44 including through communications server 60 and nurse call server 26 in the illustrative example. If the acceptance is made by the primary caregiver using one of room stations 32, the notification to the master station 38 is routed through I/O board 30 and nurse call server 26 in the illustrative example. In either case, master station 28 visually indicates on its display screen that the particular nurse call 20 has been accepted. After notification of the acceptance of the nurse call 20 at block 122, algorithm proceeds back to block 102 at the beginning of the algorithm as indicated by the circles containing the letter "A" in FIGS. 2A and 2B.

If at block 120 of algorithm 100 the primary caregiver does not accept the nurse call 20 within the relevant threshold amount of time, or if at block 116 of algorithm 100 the primary caregiver is designated as unavailable, algorithm 100 proceeds to block 124 as indicated by the circles containing the letter "B" in FIGS. 2A and 2B. At block 124, algorithm 100 determines whether the secondary caregiver is available. If at block 124 algorithm 100 determines that the secondary caregiver is available (e.g., the secondary caregiver has not been determined to be unavailable at block 104), algorithm 100 proceeds to send a message to notify the secondary caregiver of the nurse call 20, as indicated at block 126 of FIG. 2B. To reiterate, such notifications of nurse calls 20 may appear on the screens of one or more of room stations 32, master station 28, status board 50, and/or wireless communication devices 52, 54, 56, 58 carried by the secondary caregiver. In this regard, the notification of nurse call 20 may appear on the room station 32 where the secondary caregiver is determined to be located by the RTLS 12 in some embodiments.

After the secondary caregiver has been notified of the nurse call 20 at block 126 because of their availability as determined at block 124, algorithm 100 proceeds to block 128 and determines whether the nurse call 20 has been accepted by the secondary caregiver. Acceptance of the nurse call 20 by the secondary caregiver indicates that the secondary caregiver will respond to the particular nurse call 20, typically by going to the patient room from which the nurse call 20 originated or by calling the room using a nearby room station 32 or master station 28 or by using the wireless communication device 52, 54, 56, 58 carried by the caregiver. Similar to block 120 discussed above, algorithm 100 implements a timer in connection with block 128 to give the secondary caregiver a threshold amount of time, such as on the order of about two to about ten minutes, to accept the nurse call 20. The threshold amount of time of the timer associated with block 128 may or may not be the same amount of time as the timer associated with block 120 at the option of the system programmer. The discussion above of software implementation of timers is equally applicable to block 128.

If at block 128 of algorithm 100 the secondary caregiver accepts the nurse call 20 within the relevant threshold amount of time, algorithm 100 proceeds to block 122 to notify the master nurse station 28 and the patient of the acceptance of the nurse call 20. In a variant embodiment, the master nurse station 28 is notified of the secondary caregiver's acceptance of the nurse call 20, but the patient is not notified. If the acceptance by the secondary caregiver is made using one of devices 52, 54, 56, 58, the notification to the master station 38 of the acceptance is routed through network 44 including through communications server 60 and nurse call server 26 in the illustrative example. If the acceptance by the secondary caregiver is made using one of room stations 32, the notification to the master station 38 is routed through I/O board 30 and nurse call server 26 in the illustrative example. In either case, master station 28 visually indicates on its display screen that the particular nurse call 20 has been accepted. After notification of the acceptance of the nurse call 20 at block 122, algorithm 100 proceeds back to block 102 at the beginning of the algorithm as indicated by the circles containing the letter "A" in FIGS. 2A and 2B.

If at block 128 of algorithm 100 the secondary caregiver does not accept the nurse call 20 within the relevant threshold amount of time or, if at block 124 of algorithm 100 the secondary caregiver is designated as unavailable, algorithm 100 proceeds to block 130 and identifies the next closest caregiver to the room from which the nurse call 20 originated. The determination regarding the next closest caregiver is made by nurse call server 26 using information from RTLS 12, or the determination regarding the next closest caregiver is made by RTLS server 46, such as in response to a request from server 26, and then the identity of the next closest caregiver is communicated to server 26.

After the next closest caregiver to the room from which the nurse call 120 originated is determined at block 130, algorithm 100 determines whether the next closest caregiver is available as indicated at block 132. If at block 132 algorithm 100 determines that the next closest caregiver is available (e.g., the next closest caregiver has not been determined to be unavailable at block 104), algorithm 100 proceeds to send a message to notify the next closest caregiver of the nurse call 20, as indicated at block 133 of FIG. 2B. Again, such notifications of nurse calls 20 may appear on the screens of one or more of room stations 32, master station 28, status board 50, and/or wireless communication devices 52, 54, 56, 58 carried by the next closest caregiver. In this regard, the notification of nurse call 20 may appear on the room station 32 where the next closest caregiver is determined to be located by the RTLS 12 in some embodiments.

After the next closest caregiver has been notified of the nurse call 20 at block 133 because of their availability as determined at block 132, algorithm 100 proceeds to block 134 and determines whether the nurse call 20 has been accepted by the next closest caregiver. Acceptance of the nurse call 20 by the next closest caregiver indicates that the next closest caregiver will respond to the particular nurse call 20, typically by going to the patient room from which the nurse call 20 originated or by calling the room using a nearby room station 32 or master station 28 or by using the wireless communication device 52, 54, 56, 58 carried by the caregiver. Similar to blocks 120, 128 discussed above, algorithm 100 implements a timer in connection with block 134 to give the next closest caregiver a threshold amount of time, such as on the order of about two to about ten minutes, to accept the nurse call 20. The threshold amount of time of the timer associated with block 134 may or may not be the same amount of time as the timer associated with either or both of blocks 120, 128 at the option of the system programmer. The discussion above of software implementation of timers is equally applicable to block 134.

If at block 134 of algorithm 100 the next closest caregiver accepts the nurse call 20 within the relevant threshold amount of time, algorithm 100 proceeds to block 122 to notify the master nurse station 28 and the patient of the acceptance of the nurse call 20. In a variant embodiment, the master nurse station 28 is notified of the secondary caregiver's acceptance of the nurse call 20, but the patient is not notified. If the acceptance by the next closest caregiver is made using one of devices 52, 54, 56, 58, the notification to the master station 38 of the acceptance is routed through network 44 including through communications server 60 and nurse call server 26 in the illustrative example. If the acceptance by the next closest caregiver is made using one of room stations 32, the notification to the master station 38 is routed through I/O board 30 and nurse call server 26 in the illustrative example. In either case, master station 28 visually indicates on its display screen that the particular nurse call 20 has been accepted. After notification of the acceptance of the nurse call 20 at block 122, algorithm 100 proceeds back to block 102 at the beginning of the algorithm 100 as indicated by the circles containing the letter "A" in FIGS. 2A and 2B.

If at block 134 of algorithm 100 the nurse call 20 is not accepted by the next closest caregiver, or if the next closest caregiver is unavailable at block 132, algorithm 100 proceeds to block 136 to determine whether a time out or maximum number of iterations of identifying the next closest caregiver (e.g., the subsequent next closest caregiver after the previous next closest caregiver was unavailable or did not accept the nurse call 20 within the threshold amount of time) has occurred. If at block 136, the time out or maximum number of iterations has not occurred, then algorithm loops back to block 130 and proceeds from there as described above with the previous next closest caregiver being ruled out and the subsequent next closest caregiver being the one to which the steps at blocks 130, 132, 133, 134 pertain. In some embodiments, the maximum number of iterations associated with block 136 of algorithm 100 is two or three, although, any number of iterations greater than three is also within the scope of the present disclosure. In some embodiments, the time out duration associated with block 136 of algorithm 100 is about ten minutes to about 30 minutes, although a time out duration less than ten minutes or greater than 30 minutes is also within the scope of the present disclosure.

If at block 136 the time out or maximum number of iterations through blocks 130, 132, 133, 134 has occurred, algorithm 100 proceeds to block 138 and a notification is provided at the master nurse station 28 that there are no available or accepting caregivers to respond to the particular nurse call 20. At that point the nurse at the master nurse station 28 may call the patient room from which the nurse call 20 originated to speak with the patient. Alternatively or additionally, the nurse at the master nurse station 28 may physically take some other action, such as placing a direct call to the wireless communication device 52, 54, 56, 58 of a selected caregiver, even if the selected caregiver has been designated as unavailable, and order the selected caregiver to respond to the nurse call. In either scenario, algorithm 100 proceeds back to block 102 at the beginning of the algorithm 100 as indicated by the circles containing the letter "A" in FIGS. 2A and 2B.

In some embodiments, tags 42 worn by caregivers include one or more user inputs, such as buttons or touch sensors or the like, that are selectable to indicate in connection with blocks 120, 128, 134 of algorithm 100 whether the caregiver is accepting or rejecting the incoming nurse call 20. In such embodiments, if the user input rejecting the incoming nurse call 20 is selected, then algorithm 100 does not need to wait for the timers associated with blocks 120, 128, 134 to expire before proceeding on to respective blocks 124, 130, 136. Alternatively or additionally, in some embodiments, software loaded on the wireless communication devices 52, 54, 56, 58 carried by the caregivers renders one or more user inputs on the display screens of the respective device 52, 54, 56, 58 that are selectable by the caregivers to accept and/or to reject an incoming nurse call 20. In this regard, see U.S. application Ser. No. 16/143,971, which is titled "Caregiver and Staff Information System," which was filed Sep. 27, 2018, which published as U.S. Patent Application Publication No. 2019/0108908 A1, and which is already incorporated by reference herein. Selection of such user inputs on the display screens of devices 52, 54, 56, 58 operate in the same manner with regard to algorithm 100 as just described in connection with user inputs on tags 42. Alternatively or additionally, such user inputs for caregivers to indicate acceptance or rejection of incoming nurse calls 20 are displayed on graphical user interfaces (GUI's) or display screens of room stations 32 and/or beds 16 in some embodiments.

Although certain illustrative embodiments have been described in detail above, variations and modifications exist within the scope and spirit of this disclosure as described and as defined in the following claims.

The invention claimed is:

1. A system to determine caregiver availability for responding to alert calls in a healthcare facility having a plurality of patient rooms, the system comprising
 a plurality of locating tags, each of which is worn by a respective caregiver in the healthcare facility, each locating tag having tag identification data (ID) stored therein, each locating tag having a transmitter configured to transmit the respective tag ID,
 a plurality of transceivers mounted at fixed locations throughout the healthcare facility, each transceiver being configured to receive the tag ID's from the plurality of locating tags that are within a communication range of the transceiver, each transceiver having a transceiver ID stored therein,
 a locating server communicatively coupled to the plurality of transceivers to receive the tag ID's and the transceiver ID's transmitted by the plurality of transceivers and the locating server being configured to determine a location of each caregiver in the healthcare facility based on the tag ID's and the transceiver ID's,
 a plurality of alert placement devices, at least one alert placement device of the plurality of alert placement devices being located in each of the patient rooms of the plurality of patient rooms, each alert placement device being configured to send an alert call, and
 a nurse call server communicatively coupled to the plurality of alert placement devices to receive alert calls therefrom and communicatively coupled to the locating server, wherein the nurse call server is configured to send text messages to selected portable communication devices to respond to the received alerts based on the alert and the type of patient;
 a plurality of wireless access points communicatively coupled to the nurse call server and mounted within the healthcare facility configured to wirelessly communicate with a plurality of portable communication devices;
 a plurality of portable communication devices, each portable communication device being carried by a respective caregiver, wherein the portable communication devices are configured to receive software from the wireless access points which configures the portable communication devices to receive and transmit text messages to the nurse call server; wherein the plurality of portable communication devices are configured by the software to transmit available and unavailable text message responses to the nurse call server regarding the received text messages from the nurse call server; and
 wherein the nurse call server is configured to determine which caregivers of the plurality of caregivers are unavailable to respond to alert calls transmitted by the alert placement devices based on text message responses received from the plurality of portable communication devices and on a type of patient assigned to each of the patient rooms in which each of the caregivers are currently located as determined by the locating server.

2. The system of claim 1, wherein the plurality of alert placement devices comprise pillow speaker units each having a nurse call button that is selected by a respective patient to generate the alert call.

3. The system of claim 1, wherein the plurality of alert placement devices comprise patient beds each having a nurse call button that is selected by a respective patient to generate the alert call.

4. The system of claim 1, wherein the plurality of alert placement devices comprise patient beds and the alert calls comprise bed status alerts transmitted from the patient beds.

5. The system of claim 4, wherein the bed status alert from each patient bed comprises one or more of the following: a siderail position alert, a caster brake alert, a mattress alert, a bed lift system alert, a bed component temperature alert, a head of bed angle alert, or a bed height alert.

6. The system of claim 1, wherein the plurality of alert placement devices comprise patient beds including heart rate sensors and the alert calls relate to sensed heart rate.

7. The system of claim 1, wherein the plurality of alert placement devices comprise patient beds including respiration rate sensors and the alert calls relate to sensed respiration rate.

8. The system of claim 1, further comprising a plurality of room stations, each room station being located in a respective patient room of the plurality of patient rooms and communicatively coupled to the nurse call server, and the room stations are each usable to send a respective alert call.

9. The system of claim 1, wherein each patient room has a primary caregiver assigned thereto, and the nurse call server is configured to send an alert message to the portable communication device of the primary caregiver to notify the primary caregiver of any alert calls originating from any of the primary caregiver's assigned patient rooms if the primary caregiver has not been determined to be unavailable.

10. The system of claim 9, wherein each patient room has a secondary caregiver assigned thereto and if the primary caregiver has been determined to be unavailable, the nurse call server sends an alert message to the portable communication device of the secondary caregiver to notify the secondary caregiver of any alert calls originating from any of the secondary caregiver's assigned patient rooms if the secondary caregiver has not been determined to be unavailable.

11. The system of claim 10, wherein if the secondary caregiver has also been determined to be unavailable, the nurse call server sends an alert message to the portable communication device of a closest caregiver, other than the primary and secondary caregiver, determined by the locating server to be closest to the patient room from which a respective alert call has originated if the closest caregiver has not been determined to be unavailable.

12. The system of claim 11, wherein if the closest caregiver has also been determined to be unavailable, the nurse call server sends an alert message to the portable communication device of a next closest caregiver, other than the primary and secondary caregiver, determined by the locating server to be next closest to the patient room from which a respective alert call has originated if the next closest caregiver has not been determined to be unavailable.

13. The system of claim 1, wherein the nurse call server is configured also to designate caregivers as unavailable based on a qualification of the respective caregiver or the role of the respective caregiver.

14. The system of claim 1, wherein the nurse call server is configured also to designate caregivers as unavailable based on a distance between the respective caregiver and the patient room in which a respective alert call has originated exceeding a distance threshold.

15. The system of claim 1, wherein the plurality of transceivers and the plurality of locating tags communicate via ultra-wideband (UWB) signals.

16. The system of claim 15, wherein the location of the plurality of locating tags is determined by the locating server using two way ranging and/or time difference of arrival (TDOA) techniques.

17. The system of claim 15, wherein the locating server uses signals from only a subset of the plurality of transceivers to determine the location of each locating tag of the plurality of locating tags, the subset being determined based on signal strength of UWB signals between the transceivers and the respective locating tag.

18. The system of claim 17, wherein the subset comprises at least three transceivers from the plurality of transceivers having highest signal strength values as compared to others of the plurality of transceivers.

19. The system of claim 1, wherein the nurse call server is further configured to designate caregivers as unavailable if the caregivers are located in predetermined non-patient room areas of the healthcare facility, wherein the predetermined non-patient room areas of the hospital include bathrooms.

* * * * *